US011104922B2

(12) United States Patent
McCurdy et al.

(10) Patent No.: US 11,104,922 B2
(45) Date of Patent: *Aug. 31, 2021

(54) USE OF AN ESTERASE TO ENHANCE ETHYL ESTER CONTENT IN FERMENTATION MEDIA

(71) Applicant: POET Research, Inc., Sioux Falls, SD (US)

(72) Inventors: Alexander T. McCurdy, Sioux Falls, SD (US); Steven T. Bly, Sioux Falls, SD (US); Stephen M. Lewis, Sioux Falls, SD (US); Benjamin P. Gacke, Sioux Falls, SD (US); Brandon James Breitling, Sioux Falls, SD (US)

(73) Assignee: POET Research, Inc., Sioux Falls, SD (US)

(*) Notice: Subject to any disclaimer, the term of this patent is extended or adjusted under 35 U.S.C. 154(b) by 0 days.

This patent is subject to a terminal disclaimer.

(21) Appl. No.: 16/775,822

(22) Filed: Jan. 29, 2020

(65) Prior Publication Data
US 2020/0165642 A1 May 28, 2020

Related U.S. Application Data

(63) Continuation of application No. 15/988,794, filed on May 24, 2018, now Pat. No. 10,604,776.

(60) Provisional application No. 62/510,551, filed on May 24, 2017.

(51) Int. Cl.
C12P 7/64 (2006.01)
C11B 1/02 (2006.01)
C11B 13/00 (2006.01)
C11B 3/00 (2006.01)
C12N 9/20 (2006.01)
C12P 7/06 (2006.01)
A23D 9/02 (2006.01)
A23D 9/007 (2006.01)
A23D 9/04 (2006.01)

(52) U.S. Cl.
CPC ............ C12P 7/6454 (2013.01); A23D 9/007 (2013.01); A23D 9/02 (2013.01); A23D 9/04 (2013.01); C11B 1/025 (2013.01); C11B 3/003 (2013.01); C11B 3/008 (2013.01); C11B 13/00 (2013.01); C12N 9/20 (2013.01); C12P 7/06 (2013.01); C12P 7/6436 (2013.01); C12N 2330/50 (2013.01)

(58) Field of Classification Search
CPC .......... C12P 7/6454; C12P 7/06; A23D 9/02; A23D 9/007; A23D 9/04; C11B 1/025; C11B 13/00; C11B 3/003; C11B 3/008; C12N 9/20; C12N 2330/50; C11C 3/003; C12Y 302/01003; C12Y 301/01003; Y02E 50/10; Y02W 30/74
See application file for complete search history.

(56) References Cited

U.S. PATENT DOCUMENTS

| | | |
|---|---|---|
| 5,208,054 A | 5/1993 | Torii et al. |
| 6,074,863 A | 6/2000 | Svendsen et al. |
| 6,764,542 B1 | 7/2004 | Lackey et al. |
| 7,582,458 B2 | 9/2009 | Grichko |
| 7,601,858 B2 | 10/2009 | Cantrell et al. |
| 7,842,484 B2 | 11/2010 | Lewis |
| 8,476,047 B2 | 7/2013 | Burlew et al. |
| 8,608,845 B2 | 12/2013 | Naidoo et al. |
| 8,702,819 B2 | 4/2014 | Bootsma |
| 8,759,044 B2 | 6/2014 | Dicosimo et al. |
| 8,765,425 B2 | 7/2014 | Dicosimo et al. |
| 8,765,985 B2 | 7/2014 | Hora et al. |
| 9,061,987 B2 | 6/2015 | Bootsma |
| 9,139,803 B2 | 9/2015 | Redford |
| 9,290,728 B2 | 3/2016 | Bootsma |
| 9,388,100 B2 | 7/2016 | Redford |
| 9,416,274 B2 | 8/2016 | Frank |
| 9,481,794 B2 | 11/2016 | Cox |
| 9,695,449 B2 | 7/2017 | Bootsma |
| 9,896,643 B2 | 2/2018 | Redford |
| 10,113,187 B2 | 10/2018 | Bushong et al. |
| 10,167,390 B2 | 1/2019 | Cox |
| 10,526,623 B2 | 1/2020 | Bootsma |
| 10,604,776 B2 | 3/2020 | McCurdy et al. |
| 2004/0063184 A1 | 4/2004 | Grichko |
| 2008/0176298 A1 | 7/2008 | Randhava et al. |
| 2008/0314294 A1 | 12/2008 | White et al. |
| 2009/0137705 A1 | 5/2009 | Faucon Dumont et al. |
| 2010/0034586 A1 | 2/2010 | Bailey et al. |
| 2012/0060722 A1 | 3/2012 | Montpeyroux et al. |
| 2013/0157324 A1 | 6/2013 | Dicosimo et al. |
| 2014/0230693 A1 | 8/2014 | Gonzalez Leon et al. |
| 2016/0145650 A1 | 5/2016 | Lewis et al. |
| 2018/0273988 A1 | 9/2018 | Lewis et al. |

(Continued)

FOREIGN PATENT DOCUMENTS

| | | |
|---|---|---|
| BR | PI0704791 A2 | 7/2009 |
| EP | 2689006 A2 | 1/2014 |
| EP | 2264157 B1 | 5/2014 |

(Continued)

OTHER PUBLICATIONS

"U.S. Appl. No. 15/988,794, Corrected Notice of Allowability dated Jan. 27, 2020", 3 pgs.
"U.S. Appl. No. 15/988,794, Examiner Interview Summary dated Aug. 16, 2019", 2 pgs.
"U.S. Appl. No. 15/988,794, Non Final Office Action dated Apr. 19, 2019", 11 pgs.
"U.S. Appl. No. 15/988,794, Notice of Allowance dated Nov. 20, 2019", 11 pgs.
"U.S. Appl. No. 15/988,794, PTO Response to Rule 312 Communication dated Feb. 24, 2020", 2 pgs.

(Continued)

Primary Examiner — Delia M Ramirez
(74) Attorney, Agent, or Firm — Honigman LLP

(57) ABSTRACT

Methods to prepare vegetable oil compositions having an elevated ethyl ester content are provided.

18 Claims, 15 Drawing Sheets

(56) References Cited

U.S. PATENT DOCUMENTS

| | | | |
|---|---|---|---|
| 2018/0340197 | A1 | 11/2018 | Mccurdy et al. |
| 2020/0063168 | A1 | 2/2020 | Bootsma |

FOREIGN PATENT DOCUMENTS

| | | | |
|---|---|---|---|
| WO | WO-8802775 | A1 | 4/1988 |
| WO | WO-2004081193 | A2 | 9/2004 |
| WO | WO-2012109221 | A1 | 8/2012 |
| WO | WO-2015181308 | A1 | 12/2015 |
| WO | WO-2018031540 | A1 | 2/2018 |
| WO | WO-2018218033 | A2 | 11/2018 |
| WO | WO-2018218033 | A3 | 2/2019 |

OTHER PUBLICATIONS

"U.S. Appl. No. 15/988,794, Response filed Aug. 15, 2019 to Non-Final Office Action dated Apr. 19, 2019", 8 pgs.

"International Application Serial No. PCT/US2018/034410, International Preliminary Report on Patentability dated Dec. 5, 2019", 8 pgs.

"International Application Serial No. PCT/US2018/034410, International Search Report dated Jan. 17, 2019", 6 pgs.

"International Appiication Serial No. PCT/US2018/034410, Written Opinion dated Jan. 17, 2019", 6 pgs.

Bailey, Helen K., "Novel Uses of Vegetable Oil in Asphalt Mixtures", Ph.D Thesis, U. of East London, UK, (Sep. 2010), 366 pgs.

Bailey, Helen K., et al., "The Use of Vegetable Oil as a Rejuvenator for Asphalt Mixtures", 5th Eurasphalt and Eurobitume Congress, Istanbul, (Jun. 13-15, 2012), 10 pgs.

Bailey, Helen K., et al., "The Use of Vegetable Oil in Asphalt Mixtures, in the Laboratory and Field", 5th Eurasphalt and Eurobitume Congress, Istanbul, (Jun. 13-15, 2012), 12 pgs.

Bennert, Thomas, et al., "Fatigue Performance of Re-Refined Engine Oil Bottoms (REOB) Modified Asphalt—A Laboratory Study", 95th Annual Transportation Research Board Meeting, (Jan. 2016), 26 pgs.

D'Amore, Tony, et al., "A Study of Ethanol Tolerance in Yeast", Critical Reviews in Biotechnology, vol. 9:4, (1990), 18 pgs.

D'Amore, Tony, et al., "Ethanol tolerance of yeast", Enzyme and Microbial Technology, vol. 9:6, (Jun. 1987), 9 pgs.

Golalipour, Amir, "Investigation of the Effect of Oil Modification on Critical Characteristics of Asphalt Binders", PhD Dissertation, U. of Wisconsin—Madison, [Online]. Retrieved from the Internet: <URL: http://www.asphaltinstitute.org/wp-content/uploads/Thickness_Mix/PhDDissertationDocument-Final-AG2.pdf>, (2013), 204 pgs.

Hughes, Stephen R, et al., "Production of Candida antarctica lipase B gene open reading frame using automated PCR gene assembly protocol on robotic workcell and expression in an ethanologenic yeast for use as resin-bound biocatalyst in biodiesel production", Journal of the Association for Lab. Automation, 16(1), (Feb. 2011), 17-37.

Layfield, J. Blake, et al., "What Brewers Should Know About Viability, Vitality, and Overall Brewing Fitness: A Mini-Review", Master Brew. Assoc. Am., 52:3, (2015), 9 pgs.

Meng, et al., "Two-step synthesis of fatty acid ethyl ester from soybean oil catalyzed by Yarrowia lipolytica lipase", Biotechnology for Biofuels, vol. 4, No. 6, (2011), 9 pgs.

Mogawer, Walaa S., et al., "Evaluating the effect of rejuvenators on the degree of blending and performance of high RAP, RAS, and RAP/RAS mixtures", Road Materials and Pavement Design, vol. 14, No. 2, (2013), 29 pgs.

Moghaddam, Taher Baghaee, et al., "The use of rejuvenating agents in production of recycled hot mix asphalt: A systematic review", Construction and Building Materials 114, (2016), 805-816.

Moreau, Robert A., et al., "Changes in Lipid Composition During Dry Grind Ethanol Processing of Corn", Journal of the American Oil Chemist's Society, vol. 88, (Mar. 2010), 9 pgs.

Seidel, Joseph C., et al., "Rheological characterization of asphalt binders modified with soybean fatty acids", Construction and Building Materials, vol. 53, (Feb. 2014), 324-332.

Van Den Berg, Corjan, et al., "Simultaneous clostridial fermentation, lipase-catalyzed esterification, and ester extraction to enrich diesel with butyl butyrate", Biotechnology and Bioengineering, vol. 110, No. 1, (Jan. 2013), 6 pgs.

Winkler, Jill K., et al., "Phytosterol and Tocopherol Components in Extracts of Corn Distiller's Dried Grain", J. Agric. Food Chem., 55(16), (Jul. 2007), 6482-6486.

Winkler-Moser, Jill K., et al., "Antioxidant Activity of Phytochemicals from Distillers Dried Grain Oil", Journal of the American Oil Chemist's Society, vol. 86, (Mar. 2009), 1073-1082.

Winkler-Moser, Jill K., et al., "Composition and oxidative stability of crude oil extracts of corn germ and distillers grains", Industrial Crops and Products 33, (2011), 572-578.

Zaumanis, Martins, et al., "Influence of six rejuvenators on the performance properties of Reclaimed Asphalt Pavement (RAP) binder and 100% recycled asphalt mixtures", Construction and Building Materials, vol. 71, (Nov. 2014), 14 pgs.

Zaumanis, Martins, et al., "Use of Rejuvenators for Production of Sustainable High Content RAP Hot Mix Asphalt", The XXVIII International Baltic Road Conference, (2013), 10 pgs.

European Search Report for the related Application No. 18806452. 1, PCT/US201803441, dated Feb. 1, 2021, 9 pages.

W. R. Gibbons et al: "Integrated biorefineries with engineered microbes and high-value co-products for profitable biofuels production", In Vitro Cellular & Development Biology. Plant, vol. 45, No. 3, Apr. 3, 2009 (Apr. 3, 2009), pp. 218-228, XP055270849, US ISSN: 1054-5476, DOI: 10.1007/s11627-009-9202-1, 10 pages.

| LIPASE | %FAEE |
|---|---|
| CONTROL | 14.3 ± 0.8% |
| EVERSA TRANSFORM | 55.2 ± 1.0% |
| LIPOZYME CALB | 33.0 ± 6.1% |
| LIPOZYME TL | 47.8 ± 0.3% |

USE OF AN ESTERASE TO ENHANCE ETHYL ESTER CONTENT IN FERMENTATION MEDIA

CROSS-REFERENCE TO RELATED APPLICATIONS

This application is a continuation of U.S. patent application Ser. No. 15/988,794, filed May 24, 2018, which claims priority to U.S. Provisional Application Ser. No. 62/510,551, filed on May 24, 2017, which applications are incorporated herein by reference in their entirety.

BACKGROUND

Ethanol can be produced from grain-based feedstocks (e.g., corn, sorghum/milo, barley, wheat, soybeans, etc.), from sugar (e.g., sugar cane, sugar beets, etc.), or from biomass (e.g., lignocellulosic feedstocks, such as switchgrass, corn cobs and stover, wood, or other plant material).

In a conventional ethanol plant, corn is used as a feedstock and ethanol is produced from starch contained within the corn. Corn kernels are cleaned and milled to prepare starch-containing material for processing. Corn kernels can also be fractionated to separate the starch-containing material (e.g., endosperm) from other matter (such as fiber and germ). The starch-containing material is slurried with water and liquefied to facilitate saccharification, where the starch is converted into sugar (e.g., glucose), and fermentation, where the sugar is converted by an ethanologen (e.g., yeast) into ethanol. The fermentation product is beer, which comprises a liquid component, including ethanol, water, and soluble components, and a solids component, including unfermented particulate matter (among other things). The fermentation product is sent to a distillation system where the fermentation product is distilled and dehydrated into ethanol. The residual matter (e.g., whole stillage) comprises water, soluble components, oil, and unfermented solids (e.g., the solids component of the beer with substantially all ethanol removed, which can be dried into dried distillers grains (DDG) and sold, for example, as an animal feed product). Other co-products (e.g., syrup and oil contained in the syrup), can also be recovered from the whole stillage. Water removed from the fermentation product in distillation can be treated for re-use at the plant.

Various processes for recovering oil from a fermentation product are currently known in the art. Such processes, however, can be expensive, inefficient or even dangerous.

Conventional processes for recovering oil from a fermentation product can sacrifice oil quality such that the oil contains a high level of free fatty acids. The presence of a high level of free fatty acids can hamper the production of end products. Processes for producing ethanol, such as the process set forth in WO 2004/081193, produce fermentation byproducts which contain increased levels of oils while maintaining a low level of free fatty acids.

SUMMARY

The disclosure provides methods to produce an oil composition comprising vegetable oil comprising an ethyl ester content that is greater than about 2%, e.g., an ethyl ester content that is greater than about 7% or an ethyl ester content that is greater than about 18%, w/w based on the total weight of the oil composition, which increase is, at least in part, the result of the presence of an amount of an esterase, e.g., an exogenous esterase added before, during or after fermentation, or any combination thereof. In one embodiment, the esterase is added to fermentation media. In one embodiment, the esterase is added after fermentation, e.g., to the vegetable oil that has been separated from the ethanol, or to the vegetable oil and ethanol mixture obtained from the fermentation. In one embodiment, the vegetable oil optionally has one or more of: an iodine value of not greater than 125 and/or a combined moisture and insoluble content of no greater than 1.5% w/w based on the total weight of the composition; and also optionally a further component selected from the group consisting of: a lutein content of at least 50 mcg/g, a cis-lutein/zeaxanthin content of at least 10 mcg/g, an alpha-cryptoxanthin content of at least 5 mcg/g, a beta-cryptoxanthin content of at least 5 mcg/g, an alpha-carotene content of at least 0.5 mcg/g, and a cis-beta-carotene content of at least 0.1 mcg/g. In one embodiment, the vegetable oil comprises at least one fatty acid selected from the group consisting of C16 palmitic, C18 stearic, C18-1 oleic, C18-2 linoleic, and C18-3 linolenic. In one embodiment, the oil composition further comprises an unsaponifiables content of no greater than 3% w/w based on the total weight of the composition. In one embodiment, the oil composition further comprises an unsaponifiables content of no greater than 2.5% w/w based on the total weight of the composition. In one embodiment, the further component comprises a lutein content of at least 50 mcg/g, a zeaxanthin content of at least 30 mcg/g, a cis-lutein/zeaxanthin content of at least 10 mcg/g, an alpha-cryptoxanthin content of at least 5 mcg/g, a beta-cryptoxanthin content of at least 5 mcg/g, an alpha-carotene content of at least 0.5 mcg/g, a beta-carotene content of at least 1 mcg/g, a cis-beta-carotene content of at least 0.1 mcg/g, an alpha-tocopherol content of at least 50 mcg/g, a beta-tocopherol content of at least 2 mcg/g, a gamma-tocopherol content of at least 300 mcg/g, a delta-tocopherol content of at least 15 mcg/g, an alpha-tocotrienol content of at least 50 mcg/g, a beta-tocotrienol content of at least 5 mcg/g, a gamma-tocotrienol content of at least 80 mcg/g, a delta-tocotrienol content of at least 5 mcg/g, or any combination thereof. In one embodiment, the free fatty acid content is no greater than 5% w/w based on the total weight of the oil composition. In one embodiment, the ethyl ester content is greater than about 30% w/w in the total weight of the oil composition. In one embodiment, the ethyl ester content is greater than about 50% w/w in the total weight of the oil composition. In one embodiment, the ethyl ester content is greater than about 80% w/w in the total weight of the oil composition. In one embodiment, the ethyl ester content is greater than about 60% w/w in the total weight of the oil composition.

In one embodiment, a method for enhancing vegetable oil properties from vegetable sources subjected to fermentation, e.g., enhancing corn oil properties from ground corn subjected to fermentation, is provided. The method includes providing an aqueous composition comprising a vegetable source such as ground corn and a glucoamylase under conditions which produce glucose, and fermenting the glucose in the presence of yeast under conditions which produce ethanol and corn oil having an ethyl ester content that is greater than 7% w/w based on the total weight of the composition. In one embodiment, an exogenous esterase is added during fermentation. In one embodiment, an exogenous esterase is added to the fermented broth, e.g., in the beerwell. In one embodiment, the conditions include a pH of from about 3 to 6. In one embodiment, the conditions which produce glucose include one or more of: a pH of from 3 to 6, a temperature of from about 25° C. to about 40° C., or a solids content in said composition of from about 20 to 50 weight percent. In one embodiment, the conditions include maintaining a glucose concentration in the aqueous composition of less than about 2 weight percent after 12 hours of saccharification and fermentation. In one embodiment, the method produces at least 18 volume percent ethanol. In one embodiment, more than 500/o of the ground corn passes through a 0.5 mm screen. In one embodiment, a fungal acid amylase and a glucoamylase are combined with the vegetable source, e.g., ground corn. In one embodiment, the ethyl ester content is greater than about 10% w/w, greater than about 30% w/w, greater than about 50% w/w, or greater than about 60% w/w, in the total weight of the oil composition. In one embodiment, the esterase is a bacterial, yeast, plant or fungal esterase. In one embodiment, the esterase is a lipase. In one embodiment, the esterase is in an amount that is at least 0.01% w/w or at least 0.4% w/w of the weight of vegetable fat, e.g., corn fat, in the aqueous composition prior to fermentation. In one embodiment, during the production of ethanol, the pH is maintained at 3-4.5 during the first half of the fill cycle and at 4.5-6.0 during the second half of the fill cycle. In one embodiment, glucose is produced at a temperature of from about 30° C. to about 35° C., a solids content in said composition of from about 25 to 45 weight percent, an amount of said fungal acid amylase which ranges from about 0.1 to about 10 fungal acid amylase units per gram of said dry solids, and an amount of said glucoamylase to dry solids in said composition which ranges from about 0.5 to about 6 glucoamylase units per gram of said dry solids. In one embodiment, an amount of fungal acid amylase is employed which ranges from about 0.01 to about 1.0 or about 10 to about 25 fungal acid amylase units per gram of said dry solids. In one embodiment, an amount of glucoamylase is employed which ranges from about 0.05 to about 0.5 or about 6 to about 15 glucoamylase units per gram of said dry solids. In one embodiment, the glucose is fermented under conditions comprising an initial temperature of about 35° C. which temperature is decreased during fermentation to a temperature of about 30° C., and maintaining a glucose concentration in the aqueous composition of less than about 1 weight percent after 12 hours of saccharification and fermentation, wherein the production of glucose and the fermentation of glucose to ethanol is conducted simultaneously. In one embodiment, the further component comprises a lutein content of at least 50 mcg/g, a zeaxanthin content of at least 30 mcg/g, a cis-lutein/zeaxanthin content of at least 10 mcg/g, an alpha-cryptoxanthin content of at least 5 mcg/g, a beta-cryptoxanthin content of at least 5 mcg/g, an alpha-carotene content of at least 0.5 mcg/g, a beta-carotene content of at least 1 mcg/g, a cis-beta-carotene content of at least 0.1 mcg/g, an alpha-tocopherol content of at least 50 mcg/g, a beta-tocopherol content of at least 2 mcg/g, a gamma-tocopherol content of at least 300 mcg/g, a delta-tocopherol content of at least 15 mcg/g, an alpha-tocotrienol content of at least 50 mcg/g, a beta-tocotrienol content of at least 5 mcg/g, a gamma-tocotrienol content of at least 80 mcg/g, a delta-tocotrienol content of at least 5 mcg/g, or any combination thereof.

Also provided is a method for enhancing vegetable oil properties from ground plant material subjected to fermentation, comprising: providing an aqueous composition comprising ground plant material, e.g., seeds, sized such that more than 50% of the ground material passes through a 0.5 mm screen, a fungal acid amylase and a glucoamylase under conditions which produce glucose, e.g., conditions that optionally include a pH of from 3 to 6, a temperature of from about 25° C. to about 40° C. and a solids content in said composition of from about 20 to 50 weight percent, and fermenting the glucose in the presence of a yeast under conditions which produce ethanol and vegetable oil having an ethyl ester content that is greater than about 7%, e.g., greater than about 18%, w/w based on the total weight of the oil composition, wherein an exogenous esterase is added before, during or after fermentation. In one embodiment, said conditions include a pH of from about 3 to 6 and maintaining a glucose concentration in the aqueous composition of less than about 2 weight percent after 12 hours of saccharification and fermentation, wherein said method produces at least 18 volume percent ethanol. In one embodiment, the vegetable oil has a free fatty acid content of no greater than 5% w/w based on the total weight of the composition. In one embodiment, the ethyl ester content is greater than about 20% w/w in the total weight of the oil composition. In one embodiment, the ethyl ester content is greater than about 30% w/w in the total weight of the composition. In one embodiment, the ethyl ester content is greater than about 50% w/w in the total weight of the oil composition. In one embodiment, the ethyl ester content is greater than about 60% w/w in the total weight of the oil composition. In one embodiment, the esterase is a bacterial, yeast, plant or a fungal esterase. In one embodiment, the esterase is a carboxylic ester hydrolase (EC 3.1.1.3). In one embodiment, the esterase is a lipase. In one embodiment, the esterase is in an amount that is at least 0.001%, e.g., 0.01%, w/w of the weight of plant fat in the aqueous composition prior to fermentation. In one embodiment, the esterase is in an amount that is at least 0.04% w/w of the weight of plant fat in the aqueous composition prior to fermentation. In one embodiment, the esterase is in an amount that is at least 0.4% w/w of the weight of plant fat in the aqueous composition prior to fermentation. In one embodiment, the esterase is in an amount that is at least 1.0% w/w of the weight of plant fat in the aqueous composition prior to fermentation. In one embodiment, the esterase is in an amount that is at least 5.0% w/w of the weight of plant fat in the aqueous composition prior to fermentation. In one embodiment, during the production of ethanol, the pH is maintained at 3-4.5 during the first half of the fill cycle and at 4.5-6.0 during the second half of the fill cycle. In one embodiment, glucose is produced at a temperature of from about 30° C. to about 35° C., a solids content in said composition of from about 25 to 45 weight percent, an amount of said fungal acid amylase which ranges from about 0.1 to about 10 fungal acid amylase units per gram of said dry solids, and an amount of said glucoamylase to dry solids in said composition which ranges from about 0.5 to about 6 glucoamylase units per gram of said dry solids. In one embodiment, the glucose is fermented under conditions comprising an initial temperature of about 35° C. which temperature is decreased during fermentation to a temperature of about 30° C., and maintaining a glucose concentration in the aqueous composition of less than about 1 weight percent after 12 hours of saccharification and fermentation, wherein the production of glucose and the fermentation of glucose to ethanol is conducted in a simultaneous.

Further provided is a method for enhancing vegetable oil properties from ground plant material subjected to fermentation. The method includes providing an aqueous composition comprising ground plant material to have a total percent of solids between about 25% and 35% which composition is not pH adjusted. One or more enzymes, e.g., an alpha-amylase, are added to the aqueous composition and the resulting mixture is subjected to liquefaction at temperatures between about 80° C. and 90° C., and then subjected to fermentation, e.g., under conditions described herein, in the presence of an esterase, such as a lipase, thereby providing ethanol and a vegetable oil. In one embodiment, the plant material is ground corn seed. In one embodiment, the esterase is added when fermentation is initiated, after fermentation is initiated, when fermentation is complete, or any combination thereof. In one embodiment, the esterase is in an amount that is at least 0.01% w/w of the weight of plant fat in the aqueous composition prior to fermentation In one embodiment, the esterase is in an amount that is at least 0.4% w/w of the weight of plant fat in the aqueous composition prior to fermentation. In one embodiment, the esterase is in an amount that is at least 1% w/w of the weight of plant fat in the aqueous composition prior to fermentation. In one embodiment, the esterase is in an amount that is at least 4% w/w of the weight of plant fat in the aqueous composition prior to fermentation.

DETAILED DESCRIPTION

Figure 1:
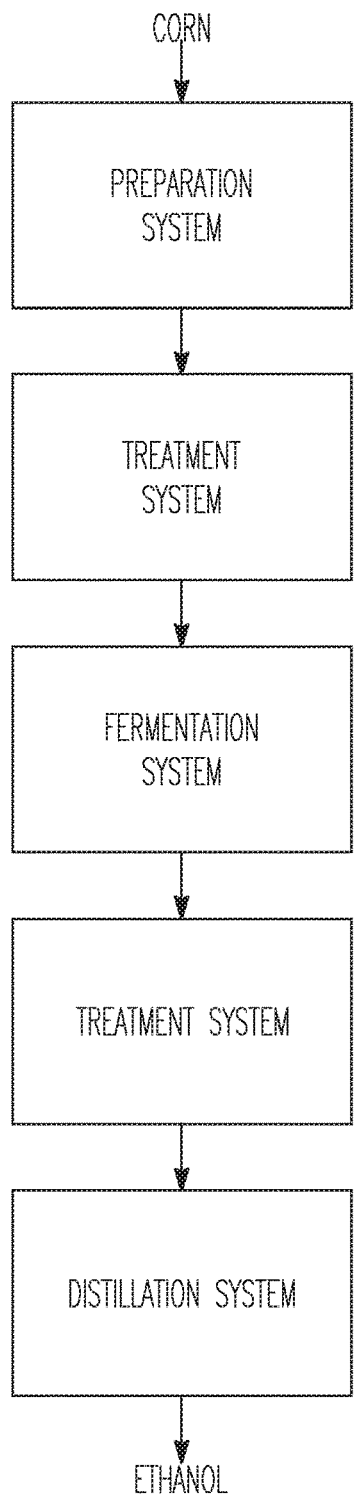
FIG. 1 is a schematic block flow diagram of a process for producing ethanol from corn.
Figure 2:
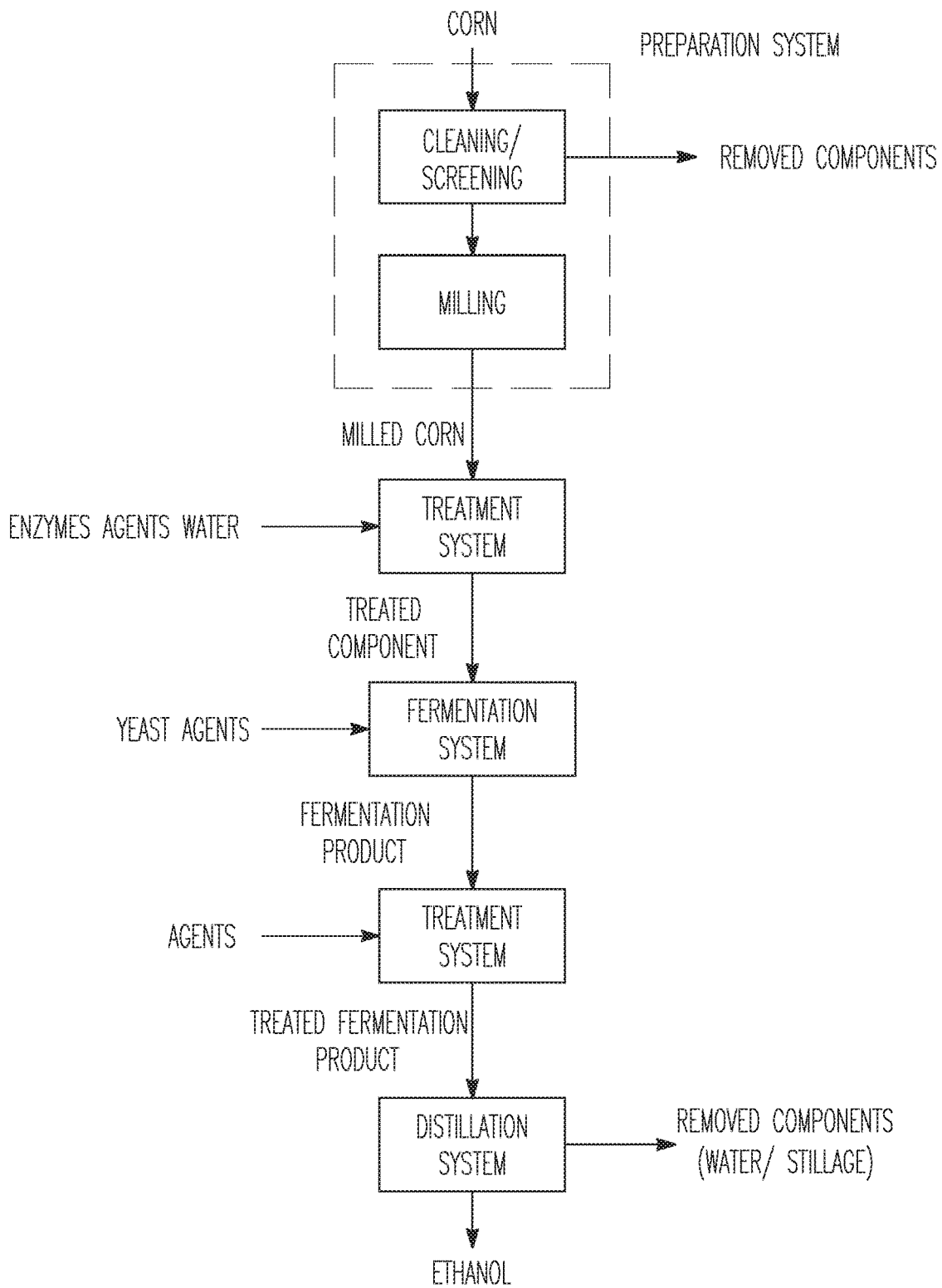
FIG. 2 is a schematic flow diagram of a process for producing ethanol from corn.

This disclosure relates to a vegetable oil, e.g., corn oil, composition with enhanced ethyl ester content and methods for producing the same.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

It must be noted that as used herein and in the appended claims, the singular forms "a", "an", and "the" include plural referents unless the context clearly dictates otherwise. Thus, for example, reference to "an alkali metal ion" includes a plurality of alkali metal ions.

Definitions

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of shall mean excluding more than trace elements of other ingredients and substantial method steps. Embodiments defined by each of these transition terms are within the scope of this invention.

As used herein, the term "about" modifying any amount refers to the variation in that amount encountered in real world conditions of producing sugars and ethanol, e.g., in the lab, pilot plant, or production facility. For example, an amount of an ingredient employed in a mixture when modified by "about" includes the variation and degree of care typically employed in measuring in an ethanol production plant or lab. For example, the amount of a component of a product when modified by "about" includes the variation between batches in an ethanol production plant or lab and the variation inherent in the analytical method. Whether or not modified by "about," the amounts include equivalents to those amounts. Any quantity stated herein and modified by "about" can also be employed in the present invention as the amount not modified by "about." For instance, the term "about" when used before a numerical designation, e.g., temperature, time, amount, and concentration, including range, indicates approximations which may vary by (+) or (−) 10%, 5% or 1%.

As used herein, the term "unrefined vegetable oil" refers to vegetable oil which has not been subjected to a refining process, such as alkali refining or physical refining (i.e., distillation, deodorization, bleaching, etc.).

As used herein, the term "free fatty acid" refers to an unesterified fatty acid, or more specifically, a fatty acid having a carboxylic acid head and a saturated or unsaturated unbranched aliphatic tail (group) of from 4 to 28 carbons. The term "aliphatic" has its generally recognized meaning and refers to a group containing only carbon and hydrogen atoms which is straight chain, branched chain, cyclic, saturated or unsaturated but not aromatic. In contrast, a fatty acid ester, such as a fatty acid ethyl ester (FAEE), is an esterified (not free) fatty acid. For example, FAEE is a fatty acid esterified with ethanol.

As used herein, the term "moisture content" refers to the amount of water and other soluble components in the oil composition. The moisture in the vegetable oil composition contains the alkali and/or alkaline metal, and may contain other soluble components, such as volatile material including hexane, ethanol, methanol, and the like.

As used herein, the term "an alkali metal ion" refers to one or more metal ion of Group 1 of the periodic table (e.g., lithium (L$^+$), sodium (Na$^+$), potassium (K$^+$), etc.).

As used herein, the term "an alkaline metal ion" refers to a metal ion of Group 2 of the periodic table (e.g., magnesium (Mg$^{2+}$), calcium (Ca$^{2+}$), etc.).

As used herein, the term "insoluble" refers to material in the oil which is not solvated by the aqueous portion, the oil or the moisture content within the oil.

As used herein, the term "unsaponifiables" refers to components of the oil that do not form soaps when blended with a base, and includes any variety of possible non-triglyceride materials. This material can act as contaminants during biodiesel production. Unsaponifiable material can significantly reduce the end product yields of the oil composition and can, in turn, reduce end product yields of the methods disclosed herein.

As used herein, the term "peroxide value" refers to the amount of peroxide oxygen (in millimoles) per 1 kilogram of fat or oil and is a test of the oxidation of the double bonds of the oils. The peroxide value is determined by measuring the amount of iodine (I$^-$) via colorimetry which is formed by the reaction of peroxides (ROOH) formed in the oil with iodide via the following equation: 2 I$^-$+H$_2$O+ROOH→ROH+2OH$^-$+I$_2$.

As used herein, the term "oxidative stability index value" refers to the length of time the oil resists oxidation at a given temperature. Typically, the oxidation of oil is slow, until the natural resistance (due to the degree of saturation, natural or added antioxidants, etc.) is overcome, at which point oxidation accelerates and becomes very rapid. The measurement of this time is the oxidative stability index value.

As used herein, the term "vegetable fermentation residue" refers to the residual components of a vegetable fermentation process after the ethanol has been recovered, typically via distillation. Typically, the vegetable fermentation residue comprises water, any residual starch, enzymes, etc.

As used herein, the term "syrup" refers to the viscous composition which is provided by the evaporation of the thin stillage.

As used herein, the term "base" refers to a compound or composition which raises the pH of an aqueous solution. Suitable bases for use in this invention include, but are not limited to, sodium hydroxide, potassium hydroxide, calcium hydroxide, or spent alkali wash solution.

As used herein, the term "alkali wash solution" refers to the basic solution which is used to disinfect the fermentor after the fermentation process has been completed. The alkali wash solution typically comprises sodium hydroxide.

As used herein, the phrase "without cooking" refers to a process for converting starch to ethanol without heat treatment for gelatinization and dextrinization of starch using alpha-amylase. Generally, for the process of the present invention, "without cooking" refers to maintaining a temperature below starch gelatinization temperatures, so that saccharification occurs directly from the raw native insoluble starch to soluble glucose while bypassing conventional starch gelatinization conditions. Starch gelatinization temperatures are typically in a range of 57° C. to 93° C. depending on the starch source and polymer type. In an embodiment of the invention, dextrinization of starch using conventional liquefaction techniques is not necessary for efficient fermentation of the carbohydrate in the grain. The present process is useful for al grain-to-ethanol processes, including cooked processes, that increase ethyl ester content via addition of exogenous esterase.

As used herein, the phrase "plant material" refers to all or part of any plant (e.g., cereal grain), typically a material including starch. Suitable plant material includes grains such as maize (corn, e.g., whole ground corn), sorghum (milo), barley, wheat, rye, rice, and millet; and starchy root crops, tubers, or roots such as sweet potato and cassava. The plant material can be a mixture of such materials and byproducts of such materials, e.g., corn fiber, corn cobs, stover, or other cellulose and hemicellulose containing materials such as wood or plant residues. Suitable plant materials include corn, either standard corn or waxy corn.

As used herein, the terms "saccharification" and "saccharifying" refer to the process of converting starch to smaller polysaccharides and eventually to monosaccharides, such as glucose. Conventional saccharification uses liquefaction of gelatinized starch to create soluble dextrinized substrate which glucoamylase enzyme hydrolyzes to glucose. In an embodiment of the invention, saccharification refers to converting raw starch to glucose with enzymes, e.g., glucoamylase and acid fungal amylase (AFAU). According to the present method, the raw starch is not subjected to conventional liquefaction and gelatinization to create a conventional dextrinized substrate. However, the methods of the invention are not limited to the use of raw starch.

As used herein, a unit of acid fungal amylase activity (AFAU) refers to the standard Novozymes units for measuring acid fungal amylase activity. The Novozymes units are described in a Novozymes technical bulletin SOP No.: EB-SM-0259.02/01. Such units can be measured by detecting products of starch degradation by iodine titration. 1 unit is defined as the amount of enzyme that degrades 5.260 mg starch dry matter per hour under standard conditions.

As used herein, a unit of glucoamylase activity (GAU) refers to the standard Novozymes units for measuring glucoamylase activity. The Novozymes units and assays for determining glucoamylase activity are described in a publicly available Novozymes technical bulletin.

As used herein, a unit of amyloglucosidase activity (AGU) refers to the standard Novozymes units for measuring amyloglucosidase activity. The Novozymes units are described in a Novozymes technical bulletin SOP No.: EB-SM-0 131.02/01. Such units can be measured by detecting conversion of maltose to glucose. The glucose can be determined using the glucose dehydrogenase reaction. 1 unit is defined as the amount of enzyme that catalyzes the conversion of 1 mmol maltose per minute under the given conditions.

Long-chain lipase units (LCLU) refers to the standard Novozymes units for measuring lipase activity. These units are described in patent application, WO 2015181308 A1. Such units can be measured by detecting the hydrolysis product, p-nitrophenol (PNP), of PNP-palmitate and measuring its resulting absorbance at 405 nm. 1 unit is defined as the amount of enzyme to release 1 µmol of PNP per minute. However, as used herein, the amount of lipase dosed in fermentation was based upon the total weight of fat within the corn present in fermentation (e.g., 0.4% lipase by weight of corn fat).

Exemplary Method for Converting Starch to Ethanol

The present disclosure provides methods for producing increased levels of ethyl esters in vegetable oil during fermentation of plant material, and to the vegetable oil composition produced thereby. The ethyl ester content resulting from fermentation may be enhanced by adding an esterase relative to the ethyl ester content in the absence of the esterase. The present disclosure also relates to methods for using the vegetable oil compositions.

The method converts starch from plant material to ethanol. In an embodiment, the present method can include preparing the plant material for saccharification, converting the prepared plant material to sugars without cooking, and fermenting the sugars.

The plant material can be prepared for saccharification by any a variety of methods, e.g., by grinding, to make the starch available for saccharification and fermentation. In an embodiment, the vegetable material can be ground so that a substantial portion, e.g., a majority, of the ground material fits through a sieve with a 0.1-0.5 mm screen. For example, in an embodiment, about 70% or more, of the ground vegetable material can fit through a sieve with a 0.1-0.5 mm screen. In an embodiment, the reduced plant material can be mixed with liquid at about 20 to about 50 wt-% or about 25 to about 45 wt-% dry reduced plant material.

The process can include converting reduced plant material to sugars that can be fermented by a microorganism such as yeast. This conversion can be effected by saccharifying the reduced plant material with an enzyme preparation, such as a saccharifying enzyme composition. A saccharifying enzyme composition can include any of a variety of known enzymes suitable for converting reduced plant material to fermentable sugars, such as amylases (e.g., α-amylase and/or glucoamylase). In an embodiment, saccharification is conducted at a pH of about 6.0 or less, for example, about 4.5 to about 5.0.

The process includes fermenting sugars from reduced plant material to ethanol. Fermenting can be effected by a microorganism, such as yeast, and as described herein may be conducted in the presence of an exogenously added esterase. In an embodiment, fermentation is conducted at a pH of about 6 or less, for example, about 4.5 to about 5. In an embodiment, the present method can include varying the pH. For example, fermentation can include filling the fermenter at pH of about 3 to about 4.5 during the first half of fill and at a pH of about 4.5 to about 6 during the second half of the fermenter fill cycle. In an embodiment, fermentation is conducted at a temperature of about 25 to about 40° C. or about 30 to about 35° C. In an embodiment, during fermentation the temperature is decreased from about 40° C. to about 30° C. or about 25° C., or from about 35° C. to about 30° C., during the first half of the fermentation, and the temperature is held at the lower temperature for the second half of the fermentation. In an embodiment, fermentation is conducted for about to 25 (e.g., 24) to about to 150 hours, for example, for about 48 (e.g., 47) to about 96 hours.

In an embodiment, the process can include simultaneously converting reduced plant material to sugars and fermenting those sugars with a microorganism such as yeast in the presence of an esterase, e.g., a lipase.

The product of the fermentation process is referred to herein as "beer." Ethanol can be recovered from the fermentation mixture, from the beer, by any of a variety of known processes, such as by distilling. The remaining stillage includes both liquid and solid material. The liquid and solid can be separated by, for example, centrifugation.

Preparing the Plant Material

The method converts starch from plant material to ethanol and vegetable oil. The plant material can be reduced by a variety of methods, e.g., by wet milling, dry grinding, or other methods of plant material reduction, to make the starch available for saccharification and fermentation. For example, vegetable material, such as kernels of corn, can be ground with a ball mill, a roller mill, a hammer mill, or another mill known for grinding vegetable material, and/or other materials for the purposes of particle size reduction. The use of emulsion technology, rotary pulsation, and other means of particle size reduction can be employed to increase surface area of plant material while raising the effectiveness of flowing the liquefied media. The prepared plant material can be referred to as being or including "raw starch."

A fine grind exposes more surface area of the plant material, or vegetable material, and can facilitate saccharification and fermentation. In an embodiment, the vegetable material is ground so that a substantial portion, e.g., a majority, of the ground material fits through a sieve with a 0.1-0.5 mm screen. In an embodiment, about 35% or more of the ground vegetable material can fit through a sieve with a 0.1-0.5 mm screen. In an embodiment, about 35 to about 70% of the ground vegetable material can fit through a sieve with a 0.1-0.5 mm screen. In an embodiment, about 50% or more of the ground vegetable material can fit through a sieve with a 0.1-0.5 mm screen. In an embodiment, about 90% of the ground vegetable material can fit through a sieve with a 0.1-0.5 mm screen. In an embodiment, all of the ground vegetable material can fit through a sieve with a 0.1-0.5 mm screen.

Fractionation

In an embodiment, the vegetable material can be fractionated into one or more components. For example, a vegetable material such as a cereal grain or corn can be fractionated into components such as fiber (e.g., corn fiber), germ (e.g., corn germ), and a mixture of starch and protein (e.g., a mixture of corn starch and corn protein). One or a mixture of these components can be fermented as described herein. Fractionation of corn or another plant material can be accomplished by any of a variety of methods or apparatus. For example, a system manufactured by Satake can be used to fractionate plant material such as corn.

Saccharification

The process can include converting reduced plant material to sugars that can be fermented by a microorganism such as yeast. This conversion can be effected by saccharifying the reduced plant material with any of a variety of known saccharifying enzyme compositions. In an embodiment, the saccharifying enzyme composition includes an amylase, such as an alpha amylase (e.g., acid fungal amylase). The enzyme preparation can also include glucoamylase. The enzyme preparation need not, and, in an embodiment, does not include protease. However, ethanol production methods can conserve water by reusing process waters (backset) which may contain protease. In an embodiment, the method employs acid fungal amylase for hydrolyzing raw starch.

Saccharifying can include a cooked liquefaction step or it can be conducted without cooking. For example, saccharifying can be conducted by mixing a source of saccharifying enzyme composition (e.g., commercial enzyme), yeast, and fermentation ingredients with ground grain and process waters without cooking.

In an embodiment, saccharifying can include mixing the reduced plant material with a liquid, which can form a slurry or suspension and adding saccharifying enzyme composition (e.g., at least one of acid fungal amylase and glucoamylase) to the liquid. In an embodiment, the method includes mixing the reduced plant material and liquid and then adding the saccharifying enzyme composition (e.g., at least one of acid fungal amylase and glucoamylase). Alternatively, adding enzyme composition can precede or occur simultaneously with mixing.

In an embodiment, the reduced plant material can be mixed with liquid at about 20 to about 50 wt-%, about 25 to about 45 (e.g., 44) wt-%, about 30 to about 40 (e.g., 39) wt-%, or about 35 wt-% dry reduced plant material. As used herein, wt-% of reduced plant material in a liquid refers to the percentage of dry substance reduced plant material or dry solids. In an embodiment, the method can convert raw or native starch (e.g., in dry reduced plant material) to ethanol at a faster rate at higher dry solids levels compared to conventional saccharification with cooking. The method may be practiced at higher dry solids levels because, unlike the conventional process, it does not include gelatinization, which increases viscosity.

Suitable liquids include water and a mixture of water and process waters, such as stillage (backset), scrubber water, evaporator condensate or distillate, side stripper water from distillation, or other ethanol plant process waters. In an embodiment, the liquid includes water. In an embodiment, the liquid includes water in a mixture with about 1 to about 70 vol-% stillage, about 15 to about 60 vol-% stillage, about 30 to about 50 vol-% stillage, or about 40 vol-% stillage.

In an embodiment, the method employs a preparation of plant material that supplies sufficient quantity and quality of nitrogen for efficient fermentation under high gravity conditions (e.g., in the presence of high levels of reduced plant material). Thus, in an embodiment, no or only low levels of stillage can suffice.

The method may produce lower viscosity stillage. Therefore, in an embodiment, increased levels of stillage can be employed without detrimental increases in viscosity of the fermentation mixture or resulting stillage.

The method may avoid temperature induced Maillard Reactions and provides increased levels of FAN in the reduced plant material, which are effectively utilized by the yeast in fermentation.

Saccharification can employ any of a variety of known enzyme sources (e.g., a microorganism) or compositions to produce fermentable sugars from the reduced plant material. In an embodiment, the saccharifying enzyme composition includes an amylase, such as an alpha amylase (e.g., acid fungal amylase) or a glucoamylase.

In an embodiment, saccharification is conducted without pH adjustment.

In an embodiment, saccharification is conducted at a pH of about 6.0 or less, pH of about 3.0 to about 6.0, about 3.5 to about 6.0, about 4.0 to about 5.0, about 4.0 to about 4.5, or about 4.5 to about 5.0. The initial pH of the saccharification mixture can be adjusted by addition of, for example, ammonia, sulfuric acid, phosphoric acid, process waters (e.g., stillage (backset), evaporator condensate (distillate), side stripper bottoms, and the like), and the like. Activity of certain saccharifying enzyme compositions (e.g., at least one of acid fungal amylase and glucoamylase) can be enhanced at pH lower than the above ranges.

In an embodiment, saccharification is conducted at a temperature of about 25 to about 40° C. or about 30 to about 35° C.

In an embodiment, saccharifying can be carried out employing quantities of saccharifying enzyme composition (e.g., at least one of acid fungal amylase and glucoamylase) selected to maintain low concentrations of dextrin in the fermentation broth. For example, the process can employ quantities of saccharifying enzyme composition (e.g., at least one of acid fungal amylase and glucoamylase) selected to maintain maltotriose (DP3) at levels at or below about 0.2 wt-% or at or below about 0.1 wt-%. For example, the present process can employ quantities of saccharifying enzyme composition (e.g., at least one of acid fungal amylase and glucoamylase) selected to maintain dextrin with a degree of polymerization of 4 or more (DP4+) at levels at or below about 1 wt-% or at or below about 0.5 wt-%. For maintaining low levels of maltotriose and/or DP4+, suitable levels of acid fungal amylase and glucoamylase include about 0.3 to about 3 AFAU/gram dry solids reduced plant material (e.g., DSC) of acid fungal amylase and about 1 to about 2.5 (e.g., 2.4) AGU per gram dry solids reduced plant material (e.g., DSC) of glucoamylase. In an embodiment, the reaction mixture includes about 1 to about 2 AFAU/gram dry solids reduced plant material (e.g., DSC) of acid fungal amylase and about 1 to about 1.5 AGU per gram dry solids reduced plant material (e.g., DSC) of glucoamylase.

In an embodiment, saccharifying can be carried out employing quantities of saccharifying enzyme composition (e.g., at least one of acid fungal amylase and glucoamylase) selected to maintain low concentrations of maltose in the fermentation broth. For example, the present process can employ quantities of saccharifying enzyme composition (e.g., at least one of acid fungal amylase and glucoamylase) selected to maintain maltose at levels at or below about 0.3 wt-%. For maintaining low levels of maltose, suitable levels of acid fungal amylase and glucoamylase include about 0.3 to about 3 AFAU/gram dry solids reduced plant material (e.g., DSC) of acid fungal amylase and about 1 to about 2.5 (e.g., 2.4) AGU per gram dry solids reduced plant material (e.g., DSC) of glucoamylase. In an embodiment, the reaction mixture includes about 1 to about 2 AFAU/gram dry solids reduced plant material (e.g., DSC) of acid fungal amylase and about 1 to about 1.5 AGU per gram dry solids reduced plant material (e.g., DSC) of glucoamylase.

Acid Fungal Amylase

In certain embodiments, the method employs an α-amylase. The α-amylase can be one produced by fungi. The α-amylase can be one characterized by its ability to hydrolyze carbohydrates under acidic conditions. An amylase produced by fungi and able to hydrolyze carbohydrates under acidic conditions is referred to herein as acid fungal amylase, and is also known as an acid stable fungal α-amylase. Acid fungal amylase can catalyze the hydrolysis of partially hydrolyzed starch and large oligosaccharides to sugars such as glucose. The acid fungal amylase that can be employed in the process can be characterized by its ability to aid the hydrolysis of raw or native starch, enhancing the saccharification provided by glucoamylase. In an embodiment, the acid fungal amylase produces more maltose than conventional (e.g., bacterial) alpha-amylases.

Suitable acid fungal amylase can be isolated from any of a variety of fungal species, including *Aspergillus, Rhizopus, Mucor, Candida, Coriolus, Endothia, Enthomophtora, Irpex, Penicillium, Sclerotium* and *Torulopsis* species. In an embodiment, the acid fungal amylase is thermally stable and is isolated from *Aspergillus* species, such as *A. niger, A. saitoi* or *A. oryzae*, from *Mucor* species such as *M. pusillus* or *M. miehei*, or from *Endothia* species such as *E. parasitica*. In an embodiment, the acid fungal amylase is isolated from *Aspergillus niger*. The acid fungal amylase activity can be supplied as an activity in a glucoamylase preparation, or it can be added as a separate enzyme. A suitable acid fungal amylase can be obtained from Novozymes, for example in combination with glucoamylase.

The amount of acid fungal amylase employed in the present process can vary according to the enzymatic activity of the amylase preparation. Suitable amounts include about 0.1 to about 10 acid fungal amylase units (AFAU) per gram of dry solids reduced plant material (e.g., dry solids corn (DSC)). In an embodiment, the reaction mixture can include about 0.3 to about 3 AFAU/gram dry solids reduced plant material (e.g., DSC). In an embodiment, the reaction mixture can include about 1 to about 2 AFAU/gram dry solids reduced plant material (e.g., DSC).

Glucoamylase

In certain embodiments, the method can employ a glucoamylase. Glucoamylase is also known as amyloglucosidase and has the systematic name 1,4-alpha-D-glucan glucohydrolase (E.C. 3.2.1.3). Glucoamylase refers to an enzyme that removes successive glucose units from the non-reducing ends of starch. For example, certain glucoamylases can hydrolyze both the linear and branched glucosidic linkages of starch, amylose, and amylopectin. A variety of suitable glucoamylases are known and commercially available. For example, suppliers such as Novozymes and Genencor provide glucoamylases. The glucoamylase can be of fungal origin.

The amount of glucoamylase employed in the present process can vary according to the enzymatic activity of the amylase preparation. Suitable amounts include about 0.1 to about 6.0 glucoamylase units (AGU) per gram dry solids reduced plant material (e.g., DSC). In an embodiment, the reaction mixture can include about 1 to about 3 AGU per gram dry solids reduced plant material (e.g., DSC). In an embodiment, the reaction mixture can include about 1 to about 2.5 (e.g., 2.4) AGU per gram dry solids reduced plant material (e.g., DSC). In an embodiment, the reaction mixture can include about 1 to about 2 AGU per gram dry solids reduced plant material (e.g., DSC). In an embodiment, the reaction mixture can include about 1 to about 1.5 AGU per gram dry solids reduced plant material (e.g., DSC). In an embodiment, the reaction mixture can include about 1.2 to about 1.5 AGU per gram dry solids reduced plant material (e.g., DSC).

Fermentation

The process includes fermenting sugars from reduced plant material to ethanol. Fermenting can be effected by a microorganism, such as yeast. In an embodiment fermentation takes place in the presence of an exogenously added esterase such as a lipase which enhances ethyl ester content of the vegetable oil obtained as a product of the fermentation. The fermentation mixture need not, and in an embodiment, does not include protease. However, the process waters may contain protease. The amount of protease can be less than that used in the conventional process. In one embodiment, fermenting is conducted on a starch composition that has not been cooked. In an embodiment, the fermentation process produces potable alcohol. Potable alcohol has only acceptable, nontoxic levels of other alcohols, such as fusel oils. Fermenting can include contacting a mixture including sugars from the reduced plant material with yeast under conditions suitable for growth of the yeast and production of ethanol. In an embodiment, fermenting employs the saccharification mixture.

Any of a variety of yeasts can be employed as the yeast starter in the present process. Suitable yeasts include any of a variety of commercially available yeasts, such as commercial strains of Saccharomyces cerevisiae. Suitable strains include "Fali" (Fleischmann's), Thermosac (Alltech), Ethanol Red (LeSafre), BioFerm AFT (North American Bioproducts), and the like. In an embodiment, the yeast is selected to provide rapid growth and fermentation rates in the presence of high temperature and high ethanol levels. In an embodiment, Fali yeast has been found to provide good performance as measured by final alcohol content of greater than 17% by volume.

The amount of yeast starter employed is selected to effectively produce a commercially significant quantity of ethanol in a suitable time, e.g., less than 75 hours.

Yeast can be added to the fermentation by any of a variety of methods known for adding yeast to fermentation processes. For example, yeast starter can be added by as a dry batch, or by conditioning/propagating. In an embodiment, yeast starter is added as a single inoculation. In an embodiment, yeast is added to the fermentation during the fermenter fill at a rate of 5 to 100 pounds of active dry yeast (ADY) per 100,000 gallons of fermentation mash. In an embodiment, the yeast can be acclimated or conditioned by incubating about 5 to 50 pounds of ADY per 10,000 gallon volume of fermenter volume in a prefermenter or propagation tank. Incubation can be from 8 to 16 hours during the propagation stage, which is also aerated to encourage yeast growth. The prefermenter used to inoculate the main fermenter is can be from 1 to 10% by volume capacity of the main fermenter, for example, from 2.5 to 5% by volume capacity relative to the main fermenter.

In an embodiment, the fermentation is conducted at a pH of about 6 or less, pH of about 3 to about 6, about 3.5 to about 6, about 4 to about 5, about 4 to about 4.5, or about 4.5 to about 5. The initial pH of the fermentation mixture can be adjusted by addition of, for example, ammonia, sulfuric acid, phosphoric acid, process waters (e.g., stillage (backset), evaporator condensate (distillate), side stripper bottoms, and the like), and the like.

Distillery yeast grow well over the pH range of 3 to 6, but are more tolerant of lower pH's down to 3.0 than most contaminant bacterial strains. Contaminating lactic and acetic acid bacteria grow best at pH of 5.0 and above. Thus, in the pH range of 3.0 to 3.5, it is believed that ethanol fermentation will predominate because yeast will grow better than contaminating bacteria.

In an embodiment, the method can include varying the pH. It is believed that varying the pH can be conducted to reduce the likelihood of contamination early in fermentation and/or to increase yeast growth and fermentation during the latter stages of fermentation. For example, fermentation can include filling the fermenter at pH of about 3 to about 4.5 during the first half of fill. Fermentation can include increasing the slurry pH to pH of about 4.5 to about 6 during the second half of the fermenter fill cycle. Fermentation can include maintaining pH by adding fresh substrate slurry at the desired pH as described above. In an embodiment, during fermentation (after filling), pH is not adjusted. Rather, in this embodiment, the pH is determined by the pH of the components during filling.

In an embodiment, the pH is decreased to about five (5) or below in the corn process waters. In an embodiment, the pH is about pH 4 (e.g., 4.1) at the start of fermentation fill and is increased to about pH 5 (e.g., 5.2) toward the end of fermentation fill. In an embodiment, the method includes stopping pH control of the mash slurry after the yeast culture becomes established during the initial process of filling the fermenter, and then allowing the pH to drift up in the corn process waters during the end stages of filling the fermenter.

In an embodiment, fermentation is conducted for about to 25 (e.g., 24) to about to 150 hours, about 25 (e.g., 24) to about 96 hours, about 40 to about 96 hours, about 45 (e.g., 44) to about 96 hours, about 48 (e.g., 47) to about 96 hours. For example, fermentation can be conducted for about 30, about 40, about 50, about 60, or about 70 hours. For example, fermentation can be conducted for about 35, about 45, about 55, about 65, or about 75 hours.

In an embodiment, fermentation is conducted at a temperature of about 25 to about 40° C. or about 30 to about 35° C. In an embodiment, during fermentation the temperature is decreased from about 40° C. to about 30° C. or about 25° C., or from about 35° C. to about 30° C., during the first half of the fermentation, and the temperature is held at the lower temperature for the second half of the fermentation. In an embodiment, the temperature can be decreased as ethanol is produced. For example, in an embodiment, during fermentation the temperature can be as high as about 99° F. and then reduced to about 79° F. This temperature reduction can be coordinated with increased ethanol titers (%) in the fermenter.

In an embodiment, the method includes solids staging. Solids staging includes filling at a disproportionately higher level of solids during the initial phase of the fermenter fill cycle to increase initial fermentation rates. The solids concentration of the mash entering the fermenter can then be decreased as ethanol titers increase and/or as the fermenter fill cycle nears completion. In an embodiment, the solids concentration can be about 40% (e.g., 41%) during the first half of the fermentation fill. This can be decreased to about 25% after the fermenter is 50% full and continuing until the fermenter fill cycle is concluded. In the above example, such a strategy results in a full fermenter with solids at 33%.

It is believed that solids staging can accelerate enzyme hydrolysis rates and encourage a rapid onset to fermentation by using higher initial fill solids. It is believed that lowering solids in the last half of fill can reduce osmotic pressure related stress effects on the yeast. By maintaining overall fermenter fill solids within a specified range of fermentability, solids staging improves the capacity of the yeast to ferment high gravity mashes toward the end of fermentation.

Esterase

In certain embodiments, the method employs an esterase defined by EC 3.1.1.1 (a carboxylic-ester hydrolase) or 3.1.1.3 (a triacylglycerol lipase).

In certain embodiments, the method employs an esterase such as a lipase. Exemplary esterases include but are not limited to lipases such as those from plant, fungi, yeast or bacteria, e.g., lipases from filamentous fungi, such as those of genera *Rhizopus*, *Mucor*, *Geotrichum*, *Aspergillus*, *Fusarium* and *Penicillium*, as well as bacteria such as *Bacillus coagulans*, *Bacillus stearothermophilus*, *Bacillus alcalophilus Pseudomonas* sp., *Pseudomonas aeruginosa*, *Burkholderia multivorans*, *Burkholderia cepacia*, *Staphylococcus caseolyticus*, and yeast such as *Candida rugosa*, *Candida tropicalis*, *Candida antarctica*, *Candida cylindracea*, *Candida parapsilopsis*, *Cadida deformans*, *Candida curvata*, *Candida valida*, *Yarrowia lipolytica*, *Rhodotorula ghltinis*, *Rhodotorula pilimornae*, *Pichia bispora*, *Pichia mexicana*, *Pichia sivicola*, *Saccharomyces cerevisiae*, *Candida wickerhamii*, *Williopsis californica*, and *Candida boidinii*. The amount of esterase may be from about 0.001% to about 25% w/w of vegetable fat, e.g., about 0.01% to about 20% w/w of vegetable fat, e.g., from about 0.02% to about 0.2% w/w of vegetable fat, about 0.04% to about 4% w/w of vegetable fat, about 2% to about 20% w/w of vegetable fat, or about 0.03% to about 0.5% w/w of vegetable fat.

Simultaneous Saccharification and Fermentation

The process can include simultaneously converting reduced plant material to sugars and fermenting those sugars with a microorganism such as yeast. Simultaneous saccharifying and fermenting can be conducted using the reagents and conditions described above for saccharifying and fermenting.

In an embodiment, saccharification and fermentation is conducted at a temperature of about 25 to about 40° C. or about 30 to about 35° C. In an embodiment, during saccharification and fermentation the temperature is decreased from about 40 to about 25° C. or from about 35 to about 30° C. during the first half of the saccharification, and the temperature is held at the lower temperature for the second half of the saccharification.

Higher temperatures early during saccharification and fermentation may increase conversion of starch to fermentable sugar when ethanol concentrations are low. This can aid in increasing ethanol yield. At higher ethanol concentrations, this alcohol can adversely affect the yeast. Thus, it is believed that lower temperatures later during saccharification and fermentation are beneficial to decrease stress on the yeast. This can aid in increasing ethanol yield.

Higher temperatures early during saccharification and fermentation may reduce viscosity during at least a portion of the fermentation. This can aid in temperature control. Lower temperatures later during saccharification and fermentation may be beneficial to reduce the formation of glucose after the yeast has stopped fermenting. Glucose formation late in fermentation can be detrimental to the color of the distillers dried grain co-product.

In an embodiment, saccharification and fermentation is conducted at a pH of about 6 or less, pH of about 3 to about 6, about 3.5 to about 6, about 4 to about 5, about 4 to about 4.5, or about 4.5 to about 5. The initial pH of the saccharification and fermentation mixture can be adjusted by addition of, for example, ammonia, sulfuric acid, phosphoric acid, process waters (e.g., stillage (backset), evaporator condensate (distillate), side stripper bottoms, and the like), and the like.

In an embodiment, saccharification and fermentation is conducted for about to 25 (e.g., 24) to about to 150 hours, about 25 (e.g., 24) to about 72 hours, about 45 to about 55 hours, about 50 (e.g., 48) to about 96 hours, about 50 to about 75 hours, or about 60 to about 70 hours. For example, saccharification and fermentation can be conducted for about 30, about 40, about 50, about 60, or about 70 hours. For example, saccharification and fermentation can be conducted for about 35, about 45, about 55, about 65, or about 75 hours.

In an embodiment, simultaneous saccharifying and fermenting can be carried out employing quantities of enzyme and yeast selected to maintain high concentrations of yeast and high levels of budding of the yeast in the fermentation broth. For example, the present process can employ quantities of enzyme and yeast selected to maintain yeast at or above about 300 cells/mL or at about 300 to about 600 cells/mL.

In an embodiment, simultaneous saccharifying and fermenting can be carried out employing quantities of enzyme and yeast selected for effective fermentation without added exogenous nitrogen; without added protease; and/or without added backset. Backset can be added, if desired, to consume process water and reduce the amount of wastewater produced by the process. In addition, the present process maintains low viscosity during saccharifying and fermenting.

For example, simultaneous saccharifying and fermenting can employ acid fungal amylase at about 0.1 to about 10 AFAU per gram of dry solids reduced plant material (e.g., DSC), glucoamylase at about 0.5 to about 6 AGU per gram dry solids reduced plant material (e.g., DSC) and an esterase as described herein. For example, simultaneous saccharifying and fermenting can employ acid fungal amylase at about 0.3 to about 3 AFAU per gram of dry solids reduced plant material (e.g., DSC), glucoamylase at about 1 to about 3 AGU per gram dry solids reduced plant material (e.g., DSC) and an esterase as described herein. For example, simultaneous saccharifying and fermenting can employ acid fungal amylase at about 1 to about 2 AFAU per gram of dry solids reduced plant material (e.g., DSC), glucoamylase at about 1 to about 1.5 AGU per gram dry solids reduced plant material (e.g., DSC) and an esterase as described herein.

In an embodiment, simultaneous saccharifying and fermenting can be carried out employing quantities of enzyme and yeast selected to maintain low concentrations of glucose in the fermentation broth. For example, the present process can employ quantities of enzyme and yeast selected to maintain glucose at levels at or below about 2 wt-%, at or below about 1 wt-%, at or below about 0.5 wt-%, or at or below about 0.1 wt-%. For example, the present process can employ quantities of enzyme and yeast selected to maintain glucose at levels at or below about 2 wt-% during saccharifying and fermenting. For example, the present process can employ quantities of enzyme and yeast selected to maintain glucose at levels at or below about 2 wt-% from hours 0-10 (or from 0 to about 15% of the time) of saccharifying and fermenting. For example, the present process can employ quantities of enzyme and yeast selected to maintain glucose at levels at or below about 1 wt-%, at or below about 0.5 wt-%, or at or below about 0.1 wt-% from hours 12-54 (or from about 15% to about 80% of the time) of saccharifying and fermenting. For example, the present process can employ quantities of enzyme and yeast selected to maintain glucose at levels at or below about 1 wt-% from hours 54-66 (or about from 80% to about 100% of the time) of saccharifying and fermenting. Suitable levels of enzyme include acid fungal amylase at about 0.3 to about 3 AFAU per gram of dry solids reduced plant material (e.g., DSC) and glucoamylase at about 1 to about 3 AGU per gram dry solids reduced plant material (e.g., DSC). For example, simultaneous saccharifying and fermenting can employ acid fungal amylase at about 1 to about 2 AFAU per gram of dry solids reduced plant material (e.g., DSC), glucoamylase at about 1 to about 1.5 AGU per gram dry solids reduced plant material (e.g., DSC) and an esterase as described herein.

In an embodiment, simultaneous saccharifying and fermenting can be carried out employing quantities of enzyme and yeast selected to maintain low concentrations of maltose (DP2) in the fermentation broth. For example, the present process can employ quantities of enzyme and yeast selected to maintain maltose at levels at or below about 0.5 wt-% or at or below about 0.2 wt-%. Suitable levels of enzyme include acid fungal amylase at about 0.3 to about 3 AFAU per gram of dry solids reduced plant material (e.g., DSC), glucoamylase at about 1 to about 3 AGU per gram dry solids reduced plant material (e.g., DSC) and an esterase as described herein. For example, simultaneous saccharifying and fermenting can employ acid fungal amylase at about 1 to about 2 AFAU per gram of dry solids reduced plant material (e.g., DSC), glucoamylase at about 1 to about 1.5 AGU per gram dry solids reduced plant material (e.g., DSC) and an esterase as described herein.

In an embodiment, simultaneous saccharifying and fermenting can be carried out employing quantities of enzyme and yeast selected to maintain low concentrations of dextrin in the fermentation broth. For example, the present process can employ quantities of enzyme and yeast selected to maintain maltotriose (DP3) at levels at or below about 0.5 wt-%, at or below about 0.2 wt-%, or at or below about 0.1 wt-%. For example, the present process can employ quantities of enzyme and yeast selected to maintain dextrin with a degree of polymerization of 4 or more (DP4+) at levels at or below about 1 wt-% or at or below about 0.5 wt-%. Suitable levels of enzyme include acid fungal amylase at about 0.3 to about 3 AFAU per gram of dry solids reduced plant material (e.g., DSC), glucoamylase at about 1 to about 3 AGU per gram dry solids reduced plant material (e.g., DSC) and an esterase as described herein. For example, simultaneous saccharifying and fermenting can employ acid fungal amylase at about 1 to about 2 AFAU per gram of dry solids reduced plant material (e.g., DSC), glucoamylase at about 1 to about 1.5 AGU per gram dry solids reduced plant material (e.g., DSC) and an esterase as described herein.

In an embodiment, simultaneous saccharifying and fermenting can be carried out employing quantities of enzyme and yeast selected to maintain low concentrations of fusel oils in the fermentation broth. For example, the present process can employ quantities of enzyme and yeast selected to maintain fusel oils at levels at or below about 0.4 to about 0.5 wt-%. Suitable levels of enzyme include acid fungal amylase at about 0.3 to about 3 AFAU per gram of dry solids reduced plant material (e.g., DSC), glucoamylase at about 1 to about 3 AGU per gram dry solids reduced plant material (e.g., DSC) and an esterase as described herein. For example, simultaneous saccharifying and fermenting can employ acid fungal amylase at about 1 to about 2 AFAU per gram of dry solids reduced plant material (e.g., DSC), glucoamylase at about 1 to about 1.5 AGU per gram dry solids reduced plant material (e.g., DSC) and an esterase as described herein.

Additional Ingredients for Saccharification and/or Fermentation

The saccharification and/or fermentation mixture can include additional ingredients to increase the effectiveness of the process. For example, the mixture can include added nutrients (e.g., yeast micronutrients), antibiotics, salts, added enzymes, and the like. Nutrients can be derived from stillage or backset added to the liquid. Suitable salts can include zinc or magnesium salts, such as zinc sulfate, magnesium sulfate, and the like. Suitable added enzymes include those added to conventional processes, such as protease, phytase, cellulase, hemicellulase, exo- and endoglucanase, xylanase, and the like.

Recovering Ethanol from the Beer

The product of the fermentation process is referred to herein as "beer". For example, fermenting corn produces "corn beer". Ethanol can be recovered from the fermentation mixture, from the beer, by any of a variety of known processes. For example, ethanol can be recovered by distillation.

The remaining stillage includes both liquid and solid material. The liquid and solid can be separated by, for example, centrifugation. The recovered liquid, thin stillage, can be employed as at least part of the liquid for forming the saccharification and fermentation mixture for subsequent batches or runs.

The recovered solids, distiller's dried grain, include unfermented grain solids and spent yeast solids. Thin stillage can be concentrated to a syrup, which can be added to the distiller's dried grain and the mixture then dried to form distiller's dried grain plus solubles. Distiller's dried grain and/or distiller's dried grain plus solubles can be sold as animal feed.

Burn-Out of Residual Starches for Subsequent Fermentation

In an embodiment, the present method can include heat treatment of the beer or stillage, e.g., between the beer well and distillation. This heat treatment can convert starches to dextrins and sugars for subsequent fermentation in a process known as burn-out. Such a treatment step can also reduce fouling of distillation trays and evaporator heat exchange surfaces. In an embodiment, heat treatment staging can be performed on whole stillage. Following enzymatic treatment of the residual starches, in an embodiment, the resulting dextrins and sugars can be fermented within the main fermentation process as recycled backset or processed in a separate fermentation train to produce ethanol.

Fractionation of Solids from Fermentation

Large pieces of germ and fiber can ferment the residual starch in the fermenter. After fermentation, the fractions could be removed prior to or after distillation. Removal can be effected with a surface skimmer before to distillation. In an embodiment, screening can be performed on the beer. The screened material can then be separated from the ethanol/water mix by, for example, centrifugation and rotary steam drum drying, which can remove the residual ethanol from the cake. In embodiments in which the larger fiber and germ pieces are removed prior to bulk beer distillation, a separate stripper column for the fiber/germ stream can be utilized. Alternatively, fiber and germ could be removed by screening the whole stillage after distillation.

In an embodiment, all the components are blended and dried together. The fiber and germ can be removed from the finished product by aspiration and/or size classification. The fiber from the DDGS can be aspirated. Removal of fiber by aspiration after drying increased the amount of oil and protein in the residual DDGS by 0.2 to 1.9% and 0.4 to 1.4%/o, respectively. The amount of NDF in the residual DDGS decreased by 0.1 to 2.8%.

In an embodiment, fractionation can employ the larger fiber and germ pieces to increase the particle size of that part of the DDGS derived from the endosperm, as well as to improve syrup carrying capacity. A ring dryer disintegrator can provide some particle size reduction and homogenization.

Continuous Fermentation

The process can be run via a batch or continuous process. A continuous process includes moving (pumping) the saccharifying and/or fermenting mixtures through a series of vessels (e.g., tanks) to provide a sufficient duration for the process. For example, a multiple stage fermentation system can be employed for a continuous process with 48-96 hours residence time. For example, reduced plant material can be fed into the top of a first vessel for saccharifying and fermenting. Partially incubated and fermented mixture can then be drawn out of the bottom of the first vessel and fed in to the top of a second vessel, and so on.

The method achieves efficient production of high concentrations of ethanol without a liquefaction or saccharification stage prior to fermentation. The method can provide low concentrations of glucose and efficient fermentation. In the present method, it appears that the glucose is consumed rapidly by the fermenting yeast cell. It is believed that such low glucose levels reduce stress on the yeast, such as stress caused by osmotic inhibition and bacterial contamination pressures. Ethanol levels greater than 18% by volume can be achieved in about 45 to about 96 hours.

Exemplary Vegetable Oil Compositions

The oil compositions contain certain levels of free fatty acids and/or ethyl esters making them valuable for use in applications including asphalt rejuvenation, bio-diesel, edible and nutraceutical applications. The oil compositions are recovered from a fermentation process.

In one embodiment, a vegetable oil such as corn oil, soybean oil, sorghum oil or wheat oil is provided by the fermentation of corn, soybean, sorghum or wheat in the production of ethanol. Referring to FIG. 1, in a typical exemplary ethanol production process, corn, for instance, can be prepared for further treatment in a preparation system. The preparation system may comprise a cleaning or screening step to remove foreign material, such as rocks, dirt, sand, pieces of corn cobs and stalk, and other unfermentable material. After cleaning/screening, the particle size of corn can be reduced by milling to facilitate further processing. The corn kernels may also be fractionated into starch-containing endosperm and fiber and germ. The milled corn or endosperm is then slurried with water, enzymes and agents to facilitate the conversion of starch into sugar (e.g., glucose). The sugar can then be converted into ethanol by an ethanologen (e.g., yeast) in a fermentation system. In one embodiment, the fermentation is carried out without creating a hot slurry (i.e., without cooking). In such an embodiment, the fermentation includes the step of saccharifying the starch composition with an enzyme composition to form a saccharified composition (e.g., without cooking). In one embodiment, the starch composition comprises water and from 5% to 60% dried solids granular starch, based on the total weight of the starch composition. In another embodiment, the starch composition comprises 10% to 50% dried solids granular starch, or 15% to 40% dried solids granular starch, or 20% to 25% dried solids granular starch, based on the total weight of the starch composition.

The fermentation product is beer, which comprises ethanol, water, oil, additional soluble components, unfermented particulate matter, etc. The fermentation product can then be distilled to provide ethanol, leaving the remaining components as whole stillage. The whole stillage can then be separated to provide a liquid component (i.e., thin stillage) and a solid component. The solid component can be dried to provide the distillers dried grain, whereas the thin stillage can be taken on to provide the oil compositions.

One aspect provides an unrefined corn oil composition having a free fatty acid content of less than about 5 weight percent; a moisture content of from about 0.2 to about 1 weight percent; and an alkali metal ion and/or alkaline metal ion content of greater than 10 ppm up to about 1000 ppm. The unrefined corn oil has not been subjected to a refining process. Such refining processes include alkali refining and/or physical refining (i.e., distillation, deodorization, bleaching, etc.), and are used to lower the free fatty acid content, the moisture content, the insoluble content and/or the unsaponifiables content.

The free fatty acid content of the unrefined corn oil composition is less than about 5 weight percent. The oil composition described herein has a free fatty acid content level that can reduce the amount of front-end refining or processing for use in various applications. In some embodiments, the free fatty acid content comprises at least one fatty acid selected from the group consisting of $C_{16}$ palmitic, $C_{18}$ stearic, $C_{18-1}$ oleic, $C_{18-2}$ linoleic, and $C_{18-3}$ linolenic (where the number after the "-" reflects the number of sites of unsaturation). In some embodiments, the free fatty acid content is less than 5 weight percent. For example, in some embodiments, the free fatty acid content is less than about 4 weight percent, or alternatively, less than about 3 weight percent, or alternatively, less than about 2 weight percent, or alternatively, less than about 1 weight percent.

Maintaining low levels of moisture is advantageous as moisture can result in the formation of free fatty acids. The unrefined corn oil composition may have a moisture content of less than about 1 weight percent. The moisture in the present corn oil composition can comprise water along with other soluble components, such as one or more alkali and/or alkaline metal, and may further contain other soluble components, such as volatile material including hexane, ethanol, methanol, and the like. The pH of the water that makes up the moisture content is, in general, alkaline (i.e., pH>7) and comprises the one or more alkali and/or alkaline metals. In some embodiments, the moisture content of the unrefined corn oil composition is from about 0.2 to about 1 weight percent, or alternatively, about or less than about 0.8 weight percent, or alternatively, about or less than about 0.6 weight percent, or alternatively, about or less than about 0.4 weight percent, or alternatively, about 0.2 weight percent. In certain embodiments, the metal ion concentration of the moisture content is about 2,000 ppm. Accordingly, an unrefined corn oil composition having from about 0.2 to about 1 weight percent would have a metal ion concentration of from about 4 ppm to about 20 ppm. Typically, the moisture content of the unrefined corn oil composition is about 0.5 weight percent having a metal ion concentration of about 2000 ppm, resulting in an ion concentration in the oil composition of about 10 ppm. In some embodiments, the unrefined corn oil composition has a metal ion concentration of greater than about 0.4 ppm, or greater than about 0.5 ppm, or greater than about 0.6 ppm, or greater than about 0.7 ppm, or greater than about 0.8 ppm, or 20 ppm.

As is stated above, the moisture content is, in general, alkaline (i.e., pH>7). Accordingly, the water content in the oil comprises an alkali metal ion and/or alkaline metal ion content of or greater than about 10 ppm. The alkali metal ion present in the composition can be any alkali metal ion and/or any alkaline metal ion, and is in some embodiments, any combination of lithium ($Li^+$), sodium ($Na^+$), magnesium ($Mg^{2+}$), potassium ($K^+$) and/or calcium ($Ca^{2+}$).

In some embodiments, the alkaline moisture content can comprise an organic base, such as ammonia and/or ammonium ions. Accordingly, in one embodiment, an unrefined corn oil composition comprises a free fatty acid content of less than about 5 weight percent; a moisture content of from about 0.2 to about 1 weight percent; and an ammonia and/or ammonium ion content of greater than about 10 ppm, or from about 4 ppm to about 20 ppm.

In some embodiments, the unrefined corn oil has an insoluble content of less than about 1.5 weight percent. The insoluble content is not solvated by the aqueous portion, the oil or the moisture within the oil, and can include material such as residual solid (e.g., corn fiber).

In some embodiments, the unrefined corn oil has an unsaponifiables content less than about 3 weight percent, or less than about 2 weight percent, or less than about 1 weight percent. Unsaponifiable matter can significantly reduce the end product yields of the oil composition and can, in turn, reduce end product yields of the methods disclosed herein. The unsaponifiables content of the oil does not form soaps when blended with a base, and includes any variety of possible non-triglyceride materials that act as contaminants during biodiesel production.

The unrefined corn oil can further comprise various other oil soluble components. It is contemplated that the amount of such components would not be so much that the unrefined corn oil composition would require refining prior to being used. Such components can include, for example, one or more of lutein, cis-lutein, zea-xanthin, alpha-cryptoxanthin, beta-cryptoxanthin, alpha-carotene, beta-carotene, cis-beta-carotene, alpha-tocopherol, beta-tocopherol, delta-tocopherol, or gamma-tocopherol, alpha-tocotrienol, beta-tocotrienol, gamma-tocotrienol, and/or delta-tocotrienol. In some embodiments, the unrefined corn oil composition has a tocopherol content less than about 1 mg/g. In some embodiments, the unrefined corn oil composition has a tocotrienol content less than about 1.3 mg/g. In some embodiments, the unrefined corn oil composition has a beta-carotene content greater than about 2 µg/g. Such components are known antioxidants and can thus provide an oxidative stability to the unrefined corn oil composition.

In an embodiment, the unrefined corn oil composition exhibits a higher level of oxidative stability than corn oils prepared via conventional methods. This can be due to any combination of factors, such as, the degree of saturation of the oil, the natural antioxidants, and the like, and can easily be determined using methods well known in the art. In some embodiments, the oxidative stability of the unrefined corn oil composition is greater than about 4 hours at a temperature of about 110° C. Further, the oxidative stability can be assessed using its peroxide value. In some embodiments, the unrefined corn oil composition exhibits a peroxide value of less than about 2 parts per million, or less than 1 part per million.

Methods of Providing Ethyl Ester Containing Oil Compositions from Fermentation Residue In one embodiment, a method for providing a vegetable oil composition from a vegetable, e.g., corn, fermentation residue includes the steps of: adjusting the pH of the vegetable, e.g., corn, fermentation residue to provide a vegetable, e.g., corn, oil layer and an aqueous layer; and separating the vegetable, e.g., corn oil layer from the aqueous layer to provide the vegetable, e.g., corn oil composition.

In one embodiment, a method for providing a vegetable, e.g., corn, oil composition from a vegetable, e.g., corn fermentation residue includes: separating the vegetable, e.g., corn, fermentation residue to provide an emulsion layer and a first aqueous layer; adjusting the pH of the emulsion layer to provide a vegetable, e.g., corn, oil layer and a second aqueous layer; and separating the vegetable, e.g., corn, oil layer from the second aqueous layer to provide the vegetable, e.g., corn, oil composition.

In some embodiments, the vegetable, e.g., corn, fermentation residue comprises whole stillage. In a fermentation process, the whole stillage is the remaining components of the beer after the ethanol has been distilled off. The whole stillage comprises a solid component and a liquid component. The liquid component of the whole stillage is referred to herein as thin stillage. In one embodiment, the whole stillage can be subjected to further processing steps to produce thin stillage. Thin stillage can be recovered from the solid component of the whole stillage by natural phase separation and decanting, or can be accelerated using methods such as centrifugation. In one embodiment, the solid component of the whole stillage can be subjected to drying to provide distillers dried grain and sold as an animal feed product. In some embodiments, the vegetable, e.g., corn, fermentation residue comprises thin stillage. In one embodiment, moisture can be removed from the thin stillage to create a concentrated fermented product, herein referred to as syrup. Moisture can be removed in a variety of ways such as, for example, through evaporation under vacuum which, in turn, can prevent fouling. Accordingly, in some embodiments, the vegetable, e.g., corn, fermentation residue comprises syrup. In some embodiments, the vegetable, e.g., corn, fermentation residue has a moisture content of between about 95% and about 60% weight percent. In some embodiments, the vegetable, e.g., corn fermentation residue has a moisture content of about 95%, or about 90%, or about 85%, or about 80%, or about 75%, or about 70%, or about 65%, or about 60% weight percent.

In an embodiment, the method optionally includes the step of separating the vegetable, e.g., corn, fermentation residue (whole stillage, thin stillage, or syrup) to provide an emulsion layer and a first aqueous layer. The step of separating can be accomplished by simply allowing the phase separation to occur over time and the oil layer decanted or by utilizing a centrifuge or a combination thereof, including, but not limited to, for example, a press, extruder, a decanter centrifuge, a disk stack centrifuge, a screen centrifuge or a combination thereof. In some embodiments, the separating does not comprise heating. In one embodiment, a continuous flow at about 4000 g is maintained. One of ordinary skill in the art will appreciate that the speed or amount of centrifugal force applied will depend on various factors such as sample size and may be adjusted appropriately depending on such factors. Suitable separators and centrifuges are available from various manufacturers.

In one embodiment, the resulting emulsion layer contains from about 20% w/w to about 70% w/w oil. In another embodiment, the emulsion layer contains from about 30% w/w to about 60% w/w oil. In yet another embodiment, the emulsion layer contains from about 40% w/w to about 50% w/w oil. The oil fraction may also comprise varying amounts of the overall fermentation residue volume. In one embodiment, the emulsion layer comprises about 20% w/w of the initial fermented product volume.

In one embodiment, the step of separating the vegetable, e.g., corn, fermentation residue is performed soon after initial production of the ethanol in order to maintain oil composition quality and prevent exposure to heat and oxygen, which are contributors to the formation of free fatty acids. The emulsion layer, which comprises the oil composition, is in one embodiment separated from the first aqueous layer. All or a fraction of the first aqueous layer may be further processed or applied to solids such as, for example, distillers dried grain.

In one embodiment, once separated from the first aqueous layer, the pH of the emulsion layer is adjusted such that the emulsion is sufficiently broken, thus providing the oil composition and a second aqueous layer. The pH adjustment allows selective separation of higher quality oil while leaving the free fatty acids in an aqueous fraction by saponifying the fatty acids thus making them more water soluble. Thus, a portion of the free fatty acid is removed resulting in oil that contains low levels of free fatty acid. The age of the fermented product and the organic acid content of the fermented product can affect the optimum pH for separation, however, the oil fraction is treated with the highest pH possible to reduce the overall free fatty acid content in the separated oil without sacrificing oil quality. Typically, suitable pH's range from about 7.5 to about 10. The mixture of the free oil composition and oil fraction can be removed for further processing.

In another embodiment, the first aqueous layer is not removed from the emulsion layer but rather is subjected to base treatment to form the oil layer and the second aqueous layer which comprises both the first aqueous layer and water resulting from breakage of the emulsion. The oil layer is then separated from the second aqueous layer. Accordingly, in some embodiments, the method comprises the steps of a) adjusting the pH of the vegetable fermentation residue to provide a corn oil layer and a second aqueous layer; and b) separating the vegetable oil layer from the second aqueous layer to provide the vegetable oil composition. In some embodiments, the separating steps do not comprise heating.

In some embodiments, the pH of the emulsion layer is lowered by adding an acid. In one such embodiment, the pH can be adjusted downward by about 1 pH unit, or about 2 pH units, or about 3 pH units. It is contemplated that any inorganic or mineral acid can be used for adjusting the pH of the emulsion layer.

In some embodiments, the pH of the emulsion layer is raised by adding base. In one such embodiment, the pH can be adjusted upward by about 1 pH unit, or about 2 pH units, or about 3 pH units, or about 4 pH units, or about 5 pH units, or about 6 pH units. In some embodiments, the pH of the emulsion layer is less than about 4, or about 3.5, prior to the step of adjusting the pH of the emulsion layer. It is contemplated that any inorganic or mineral base can be used for adjusting the pH of the emulsion layer. Suitable bases include, but are not limited to, a base selected from the group consisting of sodium hydroxide, sodium methoxide, potassium hydroxide, calcium hydroxide, or spent alkali wash solution. In some embodiments, the base can be organic base, such as ammonia. Efficient phase separation of the emulsion layer can be achieved by adjusting the pH of the emulsion layer to about 7.5 to about 10, or from about 8 to about 9, or to a pH of about 8.2.

Once the emulsion has sufficiently broken, a corn oil layer and a second aqueous layer are provided. The corn oil layer comprises the unrefined corn oil as disclosed herein.

In some cases, it may be that an interface layer is present between the oil layer and the aqueous layer, which is known in the art as a rag layer. The interface layer can comprise oil, water, phospholipids, free fatty acids, solids, etc. In some embodiments, the interface layer is substantially removed from the oil layer with the aqueous layer. However, since the interface layer can comprise a significant amount of oil, it may be advantageous to extract the oil from the interface layer. Accordingly, in some embodiments, the interface layer is kept with the oil layer and subjected to the pH adjustment step. The volume of the interface layer can be decreased by about 50% or more by using a greater volume of aqueous solution compared to the volume of the oil layer. Therefore, it may be advantageous to use a greater volume of aqueous solution by adding water and/or using spent alkali wash solution. Such methods may provide an oil having a lower phospholipid concentration.

Accordingly, the unrefined vegetable, e.g., corn, oil as disclosed herein can be provided by separating the vegetable, e.g., corn, oil layer from the second aqueous layer. The step of separating the vegetable, e.g., corn, oil layer from the second aqueous layer can be accomplished by simply allowing the phase separation to occur over time and the oil layer decanted or by utilizing centrifuge or a combination thereof, including, but not limited to, for example, a press, extruder, a decanter centrifuge, a disk stack centrifuge, a screen centrifuge or a combination thereof. In some embodiments, the separating does not comprise heating. In one embodiment, a continuous flow at about 4000 g is maintained. One of ordinary skill in the art will appreciate that the speed or amount of centrifugal force applied will depend on various factors such as sample size and may be adjusted appropriately depending on such factors. Suitable separators and centrifuges are available from various manufacturers.

In one embodiment, the second aqueous portion comprises 60% to 80% moisture, based on the total weight of the second aqueous portion. In one embodiment, the second aqueous portion comprises 10% to 40% protein, based on the total weight of the second aqueous portion. In one embodiment, the second aqueous portion comprises up to 50/o oil, based on the total weight of the second aqueous portion. The remainder of the second aqueous portion typically comprises starch, neutral detergent fiber, and the like. The second aqueous portion can be used to treat distillers dried grain or other solids where an increased level of these components is desirable.

The oil composition can be used in a wide variety of applications. Such exemplary applications include the areas of oleochemicals, feed (e.g., animal feed) as well as oils suitable for human consumption, asphalt rejuvenation, performance grade (PG) asphalt enhancement and/or bio-diesel. Accordingly, one embodiment is a recycled asphalt composition or performance-grade composition comprising the unrefined corn oil composition as described herein which may decrease the viscosity of the resulting mixture and/or enhance the properties of the pavement made therefrom, e.g., enhanced resistance to cracking, e.g., transverse cracking and age-induced surface cracking.

The oil can also be used for human consumption. Products for human consumption include edible oils that meet GRAS crude oil standards, as well as carriers for drug molecules in pharmaceutical preparations. These products fits for human consumption further include nutraceutical applications. The oil compositions described herein contain higher than average levels of various nutraceuticals such as, for example, tocopherols, tocotrienols and phytosterols. In one embodiment and while not intending to be bound to one particular theory, the oil composition's higher than average levels of various nutraceuticals may be attributable to, for example, the removal of corn oil directly from the whole kernel as opposed to simply the corn germ itself. The nutraceuticals in the present oil composition may be further processed for inclusion in various applications such as health foods, dietary supplements, food supplements, and food fortification products.

Figure 3:
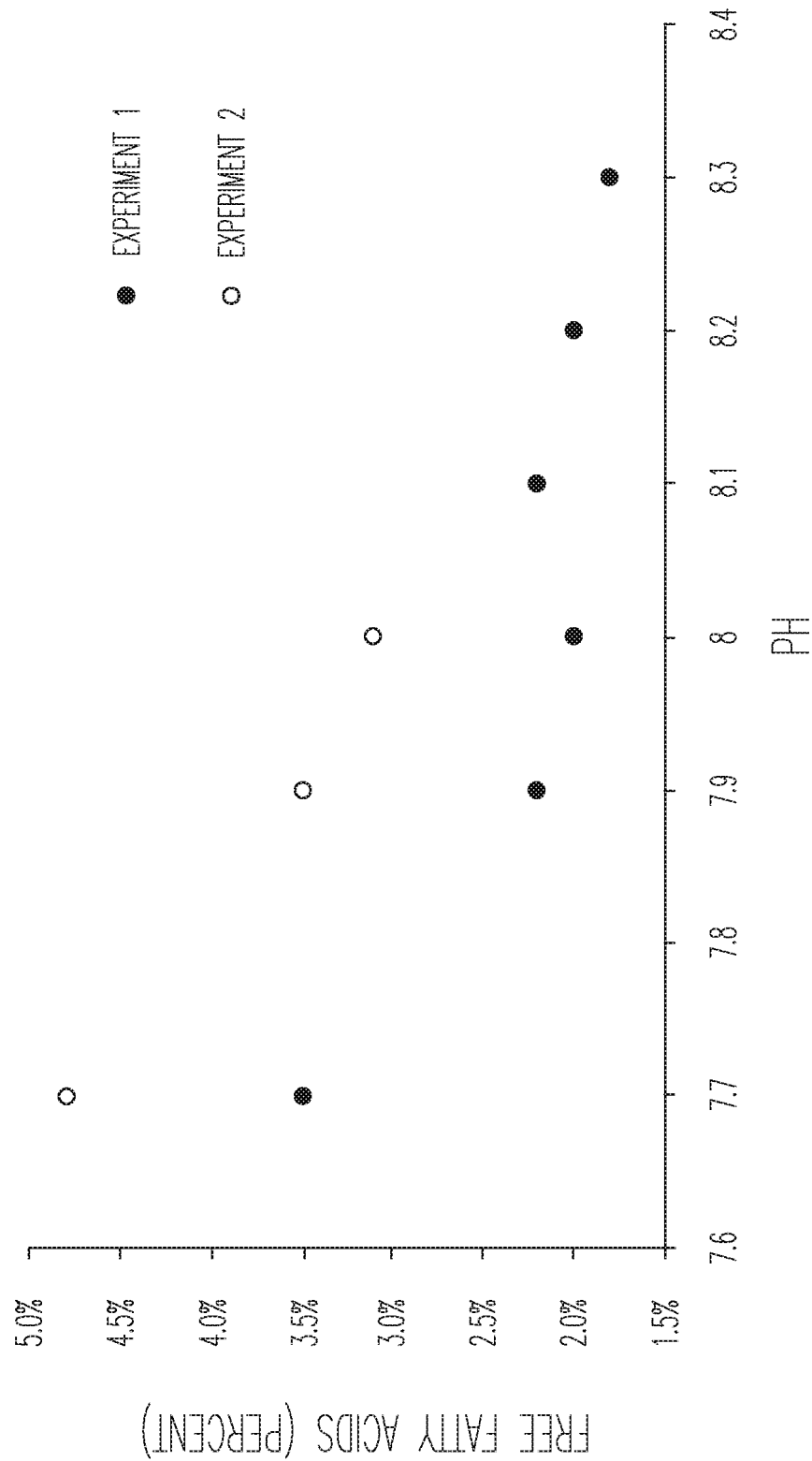
FIG. 3 shows the effect of pH on the fatty acid content of the oil composition.
Figure 4:
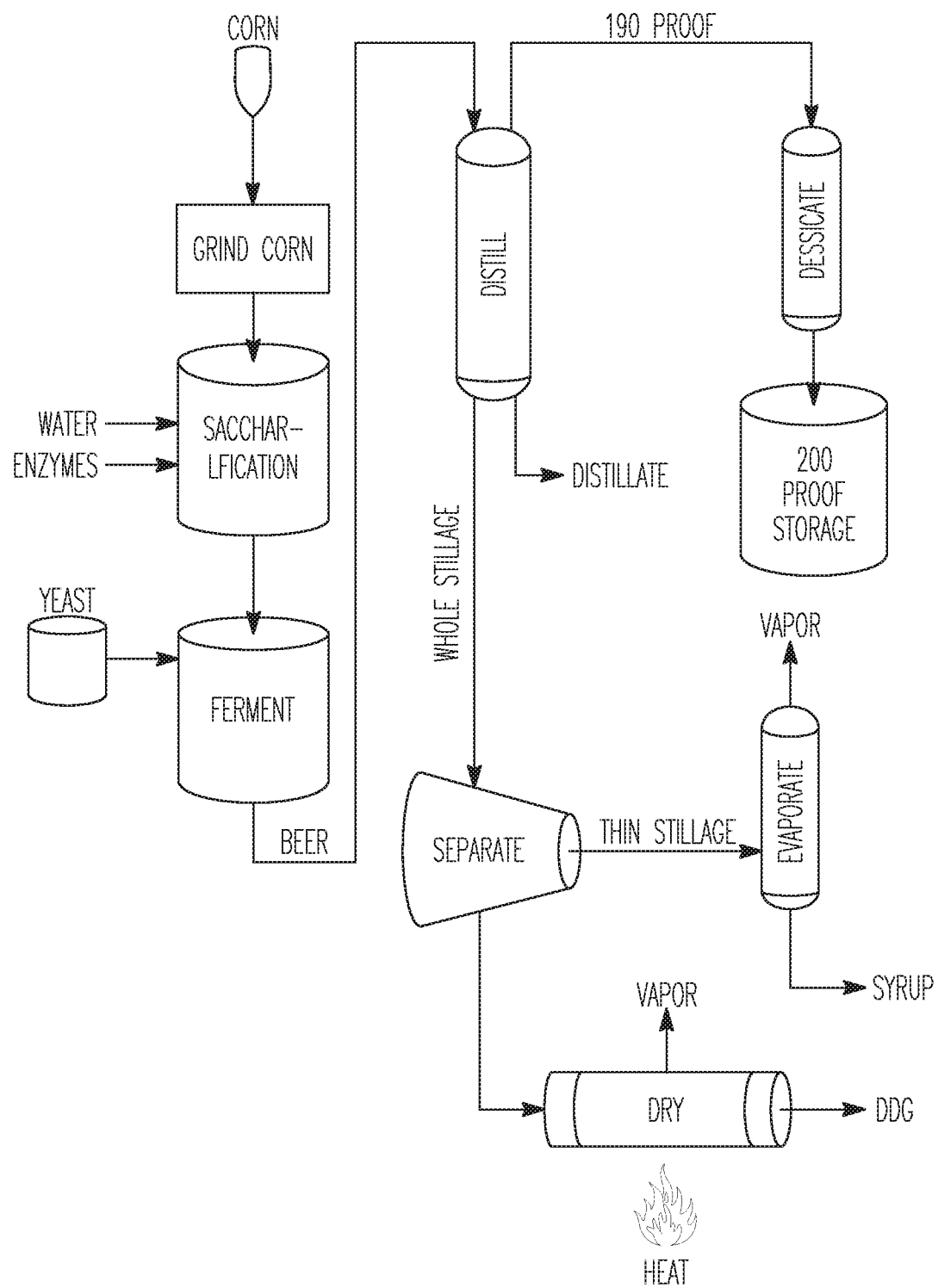
FIG. 4 shows an exemplary process flow diagram.
Figure 5A:
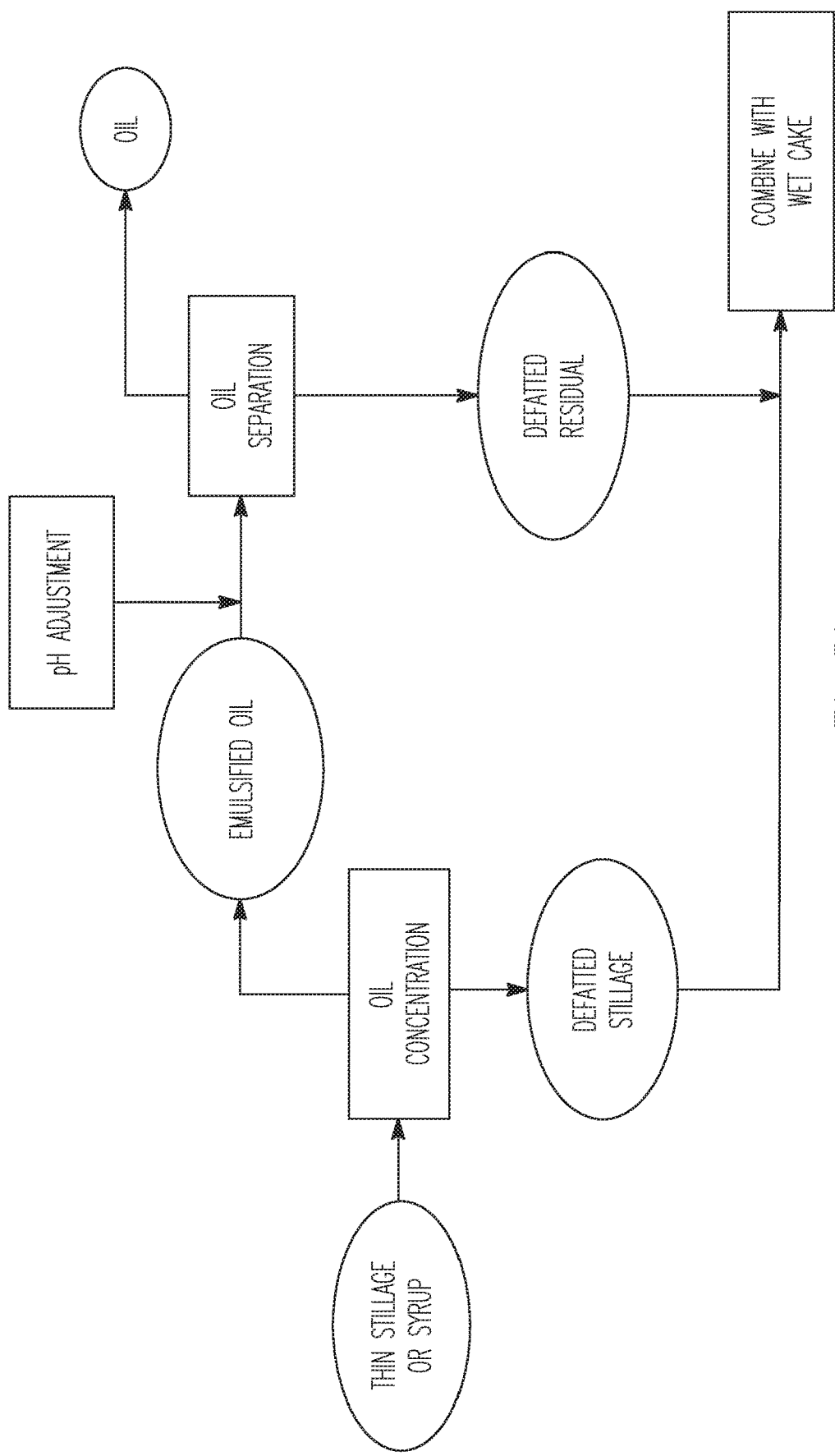
FIGS. 5A-5E show various flow diagrams for providing the oil composition and the distillers dried grains.
Figure 5B:
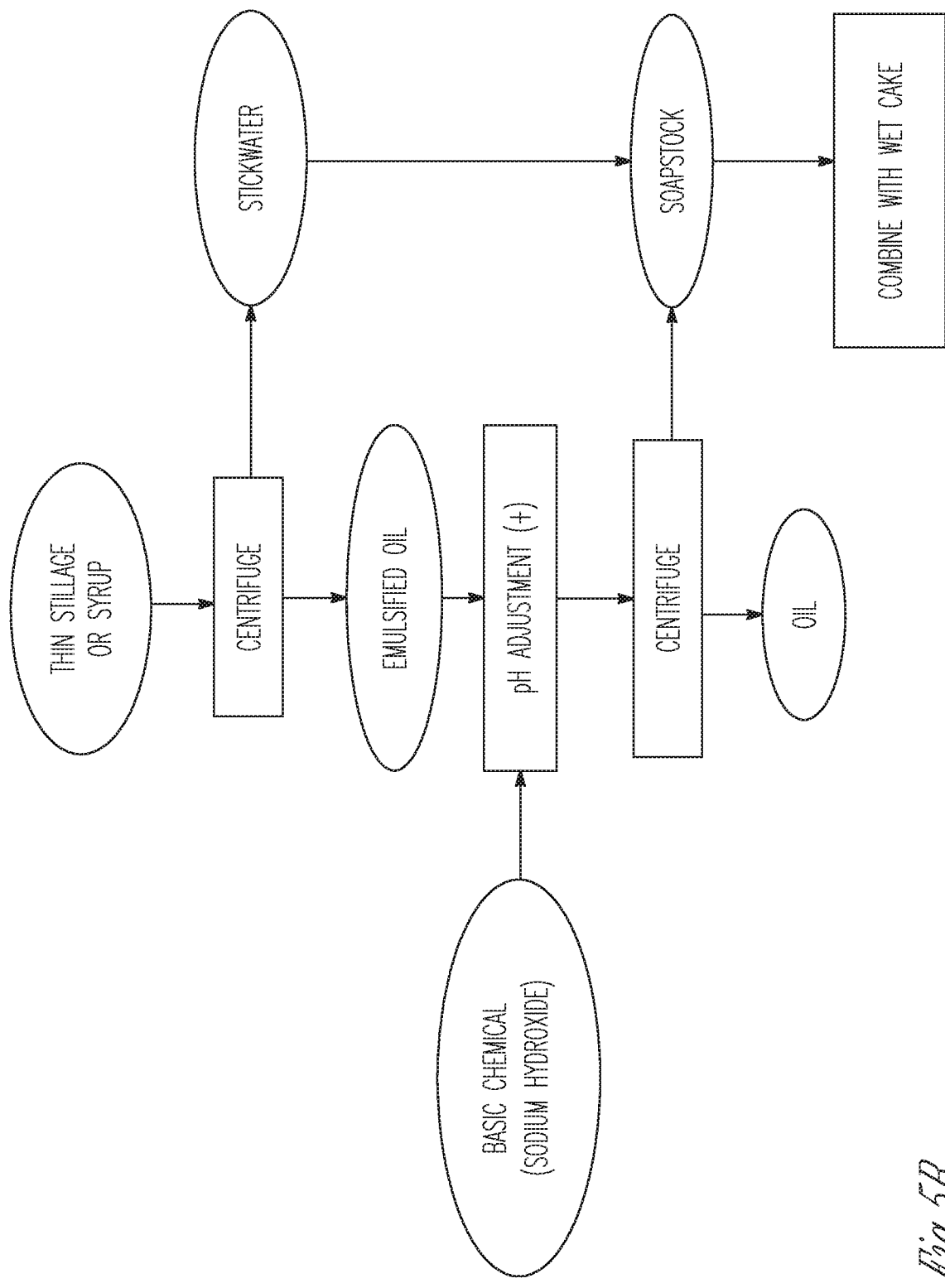
Figure 5C:
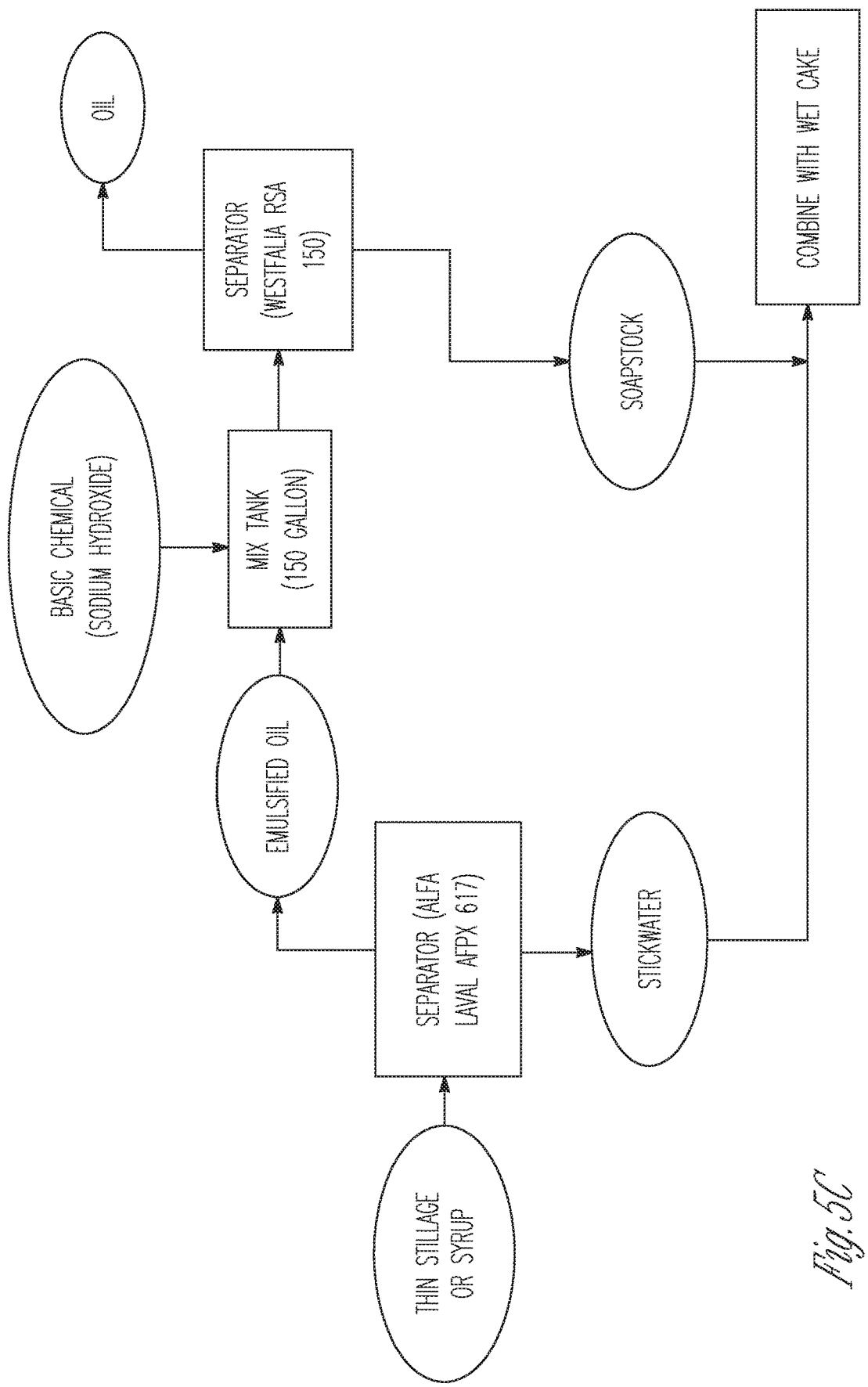
Figure 5D:
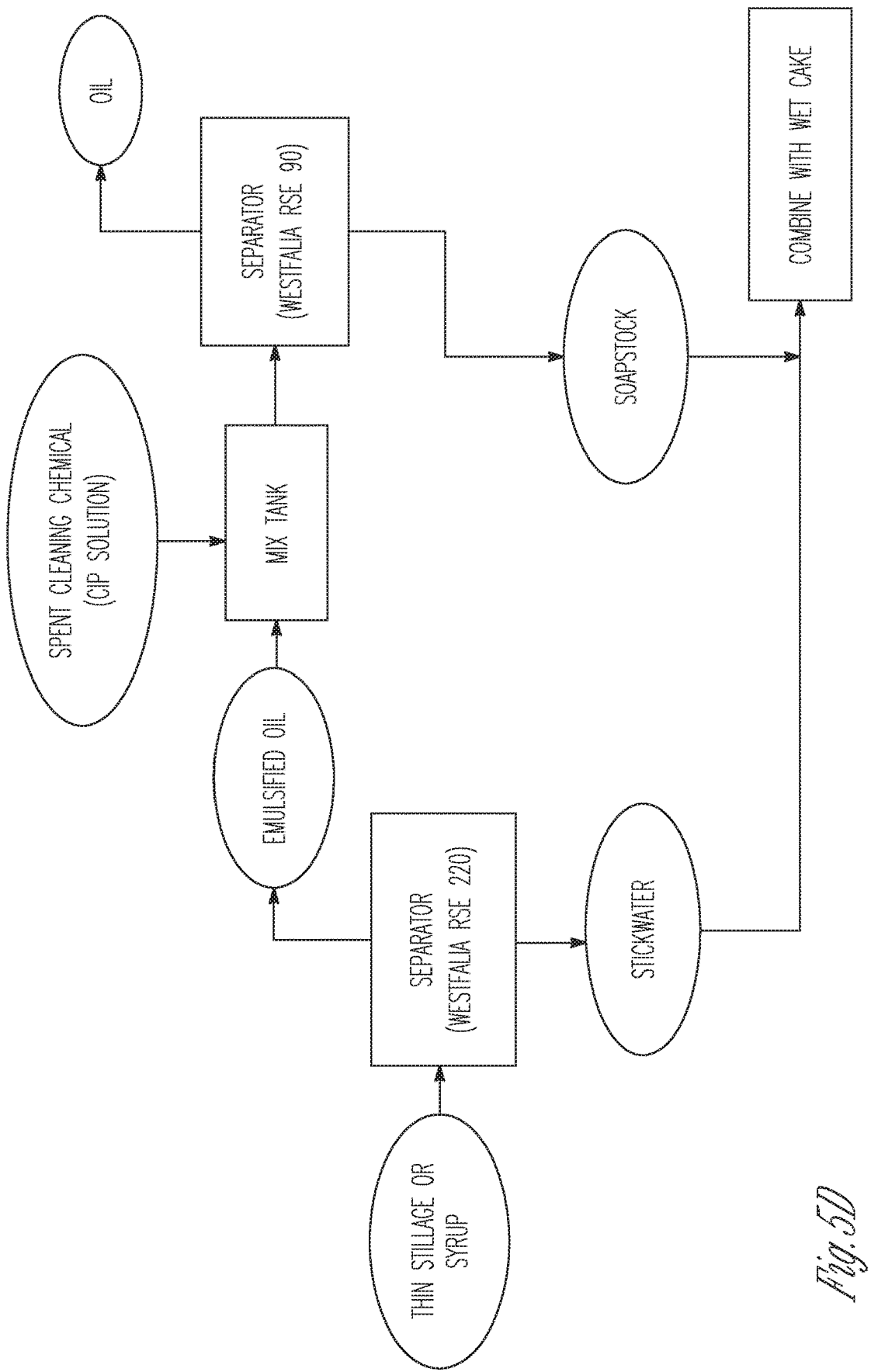
Figure 5H:
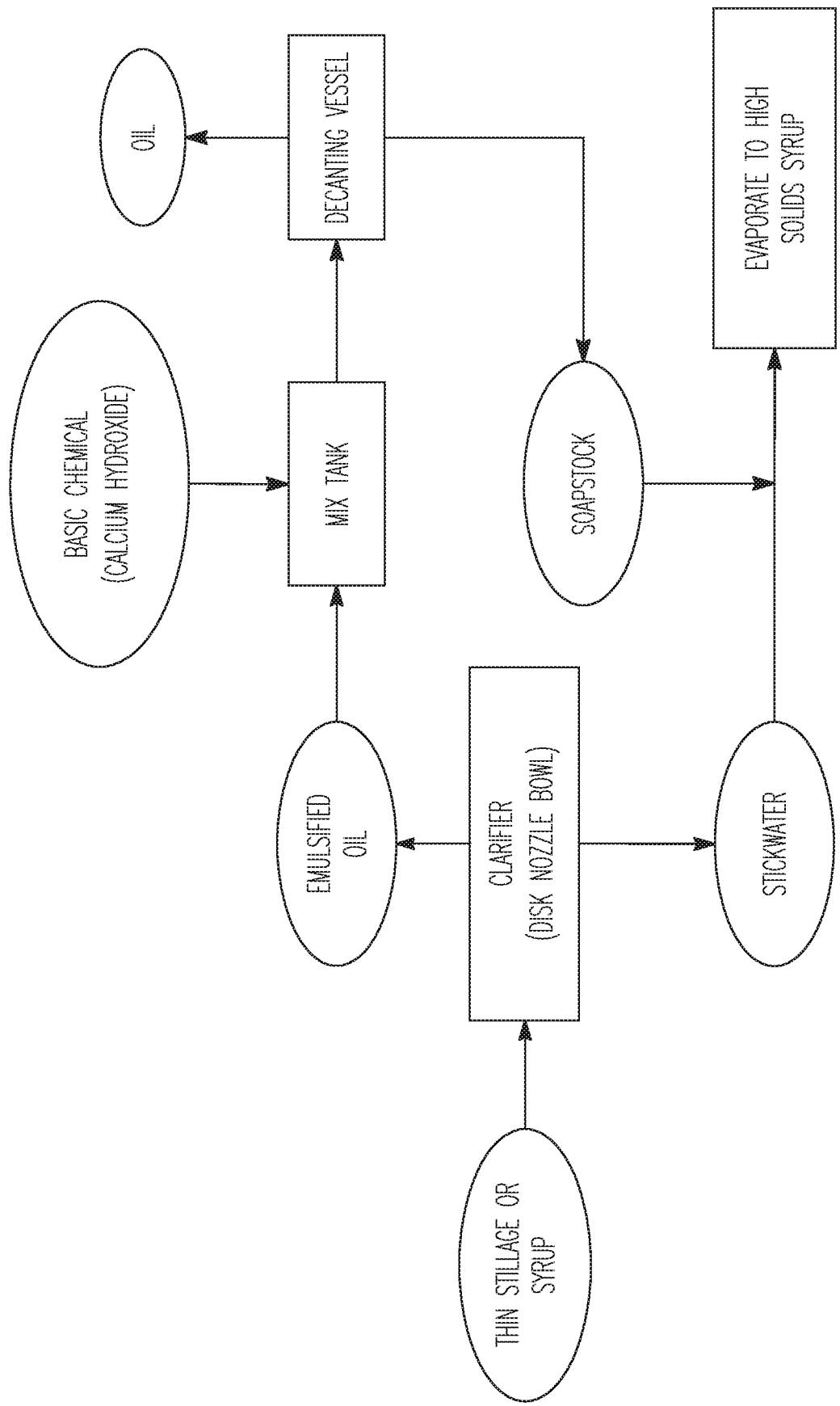
Figure 6:
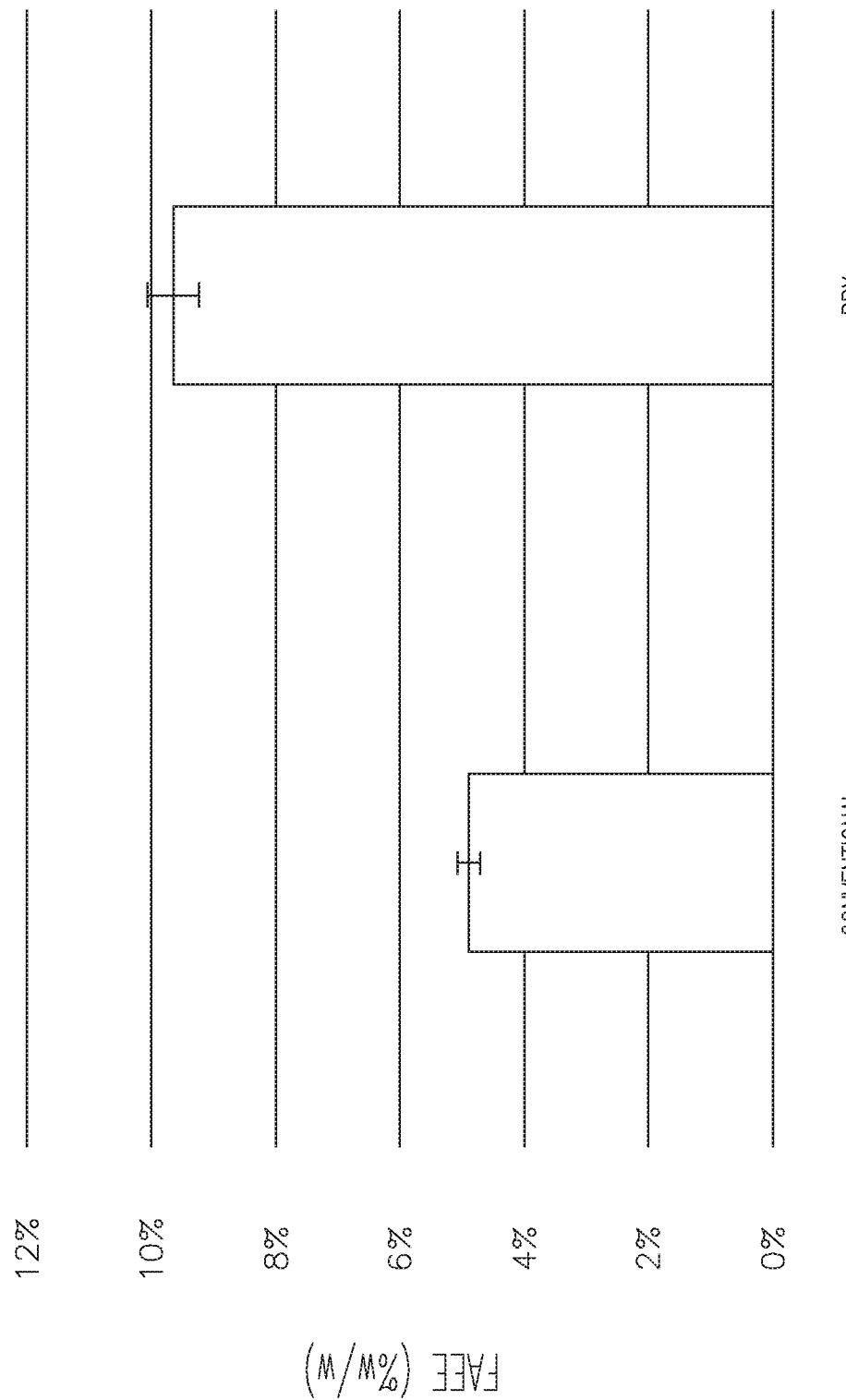
FIG. 6 shows that conventional ethanol fermentation including a liquefaction step prior to fermentation decreases the ethyl ester content of the extracted oil post fermentation compared to a control corn composition (BPX). N=5 fermentations for both conventional and BPX.

The pH level capable of providing an oil composition containing a low level of free fatty acid can be determined (FIG. 3). First, an oil fraction in the form of an emulsion separated from fermented product may be adjusted to the pH levels of 7.7, 7.9, 8.0, 8.1, 8.2, and 8.3. The samples may then be centrifuged to separate the oil composition and the oil composition was analyzed for free fatty acid content.

In summary, those samples tested at lower pH (i.e., below 8.0) exhibited free fatty acid contents above 3.5% w/w while those tested at a pH above 8.1 exhibited a free fatty acid content of below 2% w/w.

TABLE 1

| | pH | | | | | |
|---|---|---|---|---|---|---|
| | 7.7 | 7.9 | 8.0 | 8.1 | 8.2 | 8.3 |
| Free Fatty Acids (percent) Experiment 1 | 3.5 | 2.2 | 2.0 | 2.2 | 2.0 | 1.8 |
| Free Fatty Acids (percent) Experiment 2 | 4.8 | 3.5 | 3.1 | 2.2 | 2.0 | 1.8 |

A series of oil fractions, in the form of emulsions samples previously separated by a first application of a centrifugal force were treated with NaOH to adjust the pH to various levels to break the emulsion and free oil as shown in Table 2. Each sample contained the same amount of oil before adjusting the pH. After adjusting the pH to the targeted value, the volume of free oil was measured.

A pH at about 8.2 may result in the highest value of free oil volume. The volume of free oil was shown to increase up to this value and then deteriorate thereafter. Thus, an optimum pH for separation exists for each oil fraction sample.

TABLE 2

| | pH | | | | | | | | |
|---|---|---|---|---|---|---|---|---|---|
| | 7.0 | 7.4 | 7.8 | 8.0 | 8.2 | 8.4 | 8.8 | 9.2 | 10.0 |
| Free Oil (percent) Experiment 1 | 1.0 | 30 | 42 | 45 | 60 | 48 | 50 | 45 | 43 |

Experiments may be conducted to demonstrate that the combination of adjusting the pH and applying a centrifugal force resulted in (a) higher quality corn oil compositions and (b) higher corn oil composition yield compared to those oil compositions obtained upon application of a centrifugal force alone. The free fatty acid content may be shown to be reduced by up to 3% by adjusting the pH in combination with centrifugal force as opposed to centrifugal force alone. The yield of separated oil composition may be increased by 140%. The experiment was run for about 30 days, and includes 3 daily samples.

A compositional analysis of the products obtained from one embodiment of the system may be performed. The syrup fraction obtained from the ethanol production process may be centrifuged to separate into a light fraction (emulsified oil) and a heavy fraction (stickwater). The syrup obtained may be mostly free of oil. The heavy fraction may be returned to the normal process to be further evaporated and added to wet cake and dried.

The pH of the light fraction may be raised to approximately 8.2 from a pH of approximately 3.5. The pH adjusted emulsified material may be fed to a second centrifuge step. The heavy fraction (soapstock) from the second centrifuge step may be high in soaps and proteins and may be mixed with the stickwater and added to the wet cake and dried. The light fraction from the second centrifuge may be oil. The oil may exhibit a high quality and low free fatty acid content, insolubles, moisture, phospholipids and unsaponifiables. The oil may be used with or without further refining. The distiller's dried grains composition projected to result from the combination of wet cake, soapstock, and low fat syrup may exhibit lower fat and higher protein than typical for distillers dried grain.

TABLE 3

| | Fat (percent) | Protein (percent) | Moisture (percent) | Other (percent)*** |
|---|---|---|---|---|
| Starting Material* | 5.4 | 4.1 | 80 | 10 |
| First Light Fraction (Emulsified Oil)* | 35 | 3.6 | 55 | 6.8 |
| First Heavy Fraction (Stickwater)* | 3.5 | 4.2 | 83 | 10 |
| Second Light Fraction (Oil Composition)* | 98 | 0.0 | 0.8 | 1.6 |
| Second Heavy Fraction (Soapstock)* | 5.5 | 5.9 | 77 | 11 |
| Low Fat DDGS** | 4.0 | 30 | 8.7 | 57 |

*= Sampled,
**= Projected,
***= Includes fiber, ash, starch, etc.

In a conventional dry-grind ethanol process, whole corn is ground to a flour, mixed with water and cooked at a high temperature to gelatinize the starch and to make it more available for subsequent liquefaction and saccharification by enzymes. The cooked mash is then cooled to facilitate fermentation of the sugars into ethanol. The resulting beer includes soluble and insoluble components, such as proteins, oil, fiber, residual starch and glycerol. The beer is separated into ethanol and whole stillage in distillation. The whole stillage can be dewatered to produce wet cake by removing a thin stillage component by centrifugation. The oil partitions fairly equally, by weight, between thin stillage and the wet cake. Thin stillage is typically further evaporated into syrup, which can be added back onto the wet cake during a drying process that produces distillers dried grains with solubles (i.e., DDGS). Corn oil can be recovered from the syrup by a simple centrifuging step, as described for example in U.S. Pat. No. 7,601,858.

Some dry-grind ethanol processing facilities utilize a modified dry grind process known as raw starch ethanol production. In these facilities, the corn is ground to fine flour, mixed with water and enzymes, and fermented to ethanol-containing beer in a simultaneous saccharification and fermentation reaction. The rest of the raw starch process is similar to the conventional process. However, in the raw starch process the oil cannot be separated from the syrup by a simple centrifugation step, but requires an additional treatment step (pH adjustment) and a second centrifugation step to recover the oil. Overall, raw starch ethanol production requires less energy and cooling water.

Oil extracted from corn DDGS using solvents, and oil extracted centrifugally from thin stillage have similar, or slightly lower concentrations of tocopherols than corn germ oil, but have higher concentrations of phytosterols, tocotrienols, and steryl ferulates, than corn germ oil. However, the oils may also tend to have high free fatty acid composition.

The following provides exemplary methods and analyses of vegetable oil compositions.

Materials and Methods
Chemicals

Dry chemicals (ACS grade or better) were obtained from Sigma-Supelco (St. Louis, Mo.) unless otherwise noted in referenced methods. Solvents were HPLC grade and were obtained from Fisher (Fairlawn, N.J.).

Oils

The five oils that were characterized included hexane Soxhlet extracts of corn germ (CG) and DDGS (DDGS), and three oils that were centrifugally extracted from dry grind ethanol production facilities (CS-1, CS-2, CS-3). The corn germ was obtained from an ethanol production facility that operates a dry fractionation process where the corn kernels are separated into germ, fiber, and endosperm fractions prior to fermentation. Corn DDGS was obtained from a raw starch ethanol production facility operated by POET, LLC (Sioux Falls, S.D.). CG and DDGS were extracted overnight (about 20 hr) by Soxhlet extraction using hexane. Four parallel Soxhlet extractors with about 100 g/thimble were used several days in a row and the extracts were combined to obtain enough oil from the germ and DDGS for analyses and storage studies. Hexane was removed by rotary evaporation at 40° C., oil was then stirred for 4 hours under a high vacuum to remove any excess hexane, after which the oil was put into several amber bottles, topped with argon to prevent lipid oxidation, and frozen at −20° C. until used for analyses. CS-1 was obtained from a conventional dry grind ethanol plant. CS-2 and CS-3 were obtained from two different production runs from a raw starch ethanol production facility operated by POET. CS-1, CS-2, and CS-3 were shipped overnight, on dry ice, to the research location, and immediately transferred to glass bottles, topped with argon, and frozen (−20° C.) until used for analyses.

Oil Analysis
Acid Value

Acid Value was determined by titration using AOCS official method Cd 3d-63 (AOCS, 1998). The acid value was used to calculate the percent free fatty acids (FFA) as percent oleic acid by dividing the acid value by 1.99 as stated in the method. Each oil was analyzed in triplicate for Acid Value and the mean is reported.

Fatty Acid Composition and Iodine Value

Oil triacylglycerols were transesterified using the method described by Ichihara (1996). Fatty acid methyl esters were analyzed in triplicate by GC. The Iodine Values were calculated based on the fatty acid composition according to the AOCS Method Cd 1c-85 (AOCS, 1998).

Tocopherols, Phytosterols, and Steryl Ferulate Analysis

The contents of tocopherols, tocotrienols, and steryl ferulates were analyzed in triplicate in the crude oils by HPLC with a combination of UV and fluorescence detection as previously described (Winkler et al., 2007). In order to analyze total phytosterol content and composition, the oils were saponified, and the phytosterols were extracted and derivatized as previously described (Winkler et al., 2007). Phytosterols were quantitated by GC as described by Winkler and Vaughn (2009). The identity of phytosterol peaks was confirmed by GC-MS analysis performed on an Agilent (Santa Clara, Calif., USA) 6890 GC-MS equipped with a HP-5MS capillary column (30 m 9 0.25 mm 9 0.25 lm), a 5973 mass selective detector, and an 7683 autosampler. The transfer line from GC to the MSD was set to 280° C. The injector and oven temperature programs were the same as described above for the GC-FID instrument. MSD parameters were as follows: scan mode, 50-600 amu, ionizing voltage, 70 eV, and EM voltage, 1,823 V. Mass spectral identification was performed using the Wiley MS database combined with comparison to literature values for relative RT (compared to β-sitosterol) and mass spectra (Beveridge et al., 2002).

Carotenoid Analysis

Carotenoid analysis and quantitation were conducted by HPLC as described by Winkler and Vaughn (2009).

Oxidative Stability Index

The OSI at 110° C. was determined in triplicate following the AOCS Official Method Cd 12b-92 (AOCS, 1998). A Metrohm (Herisau, Switzerland) 743 Rancimat with software control automatically controlled air flow and temperature and calculated the OSI values based on induction time.

Accelerated Storage Study

The study protocol followed AOCS Recommended Practice Cg 5-97 (AOCS, 1998). Oil samples (5 g) were weighed into 40-ml amber glass vials which were loosely capped. For each treatment and day, triplicate vials were prepared. Vials were stored in completely randomized order in a dark oven held at 40±1° C. For each oil, three vials were removed on days one through six and on day eight. CG oil samples were also removed on days 10 and 12. However, as the study progressed, it was determined that the DDGS and CS-2 oils were oxidizing more slowly than the CG oil, so samples were removed on days 12 and 14 order to extend their storage by two more days. Upon removal from the oven, vials were immediately topped with argon, tightly capped, and frozen (−20° C.) until analysis. Analyses were conducted either on the same day or within 2 days of removal from the oven. Peroxide values were determined using the method described by Shantha and Decker (1994). Each oil replicate from the storage studies was analyzed in duplicate. Hexanal in the oil headspace of each replicate was quantified in duplicate by solid-phase microextraction (SPME) and GC analysis as described by Winkler and Vaughn (2009).

Room Temperature Storage Study

CS-2 oil was placed into three, 4 L amber bottles. Each bottle was filled to the same volume level of 3.4 L. The amount of headspace above the oil samples amounted to 0.9 L. Bottles were tightly capped and stored in the dark at 20° C.+3° C., the temperature was monitored daily and the high and low temperature was recorded. Samples were taken once a week for 13 weeks. To sample, bottles were first gently shaken for 30 seconds to mix the contents. Then a glass pipet was inserted into the center of the bottle and 5 ml oil was taken and placed into a screw cap vial, covered with argon, and frozen (−20° C.) until analysis. Peroxide value and headspace analysis of hexanal were performed on the oil samples as described above, and were typically run on the same day or within 1-2 days of sampling.

used to dry the wet grains may have contributed to the increase in FFA. In one experiment, Moreau et al. (2010) demonstrated that oil extracted from thin stillage and distillers dried grains (prior to mixing the grains with the syrup) had high FFA content that carried through to the DDGS. The FFA content of hexane extracted corn germ was 3.8%, which is slightly higher than the average of 2.5% FFA typically found in crude corn germ oil. For biodiesel production, oil with an Acid Value greater than one requires pretreatment because the free fatty acids form soaps during base-catalyzed esterification, which interfere with the separation of the glycerol from the fatty acid methyl esters. Thus, crude oils with lower free fatty acids will have lower oil loss due to the pre-treatment. Free fatty acids decrease the oxidative stability of oils and can also precipitate at ambient temperatures, both of which could negatively impact fuel performance.

TABLE 4

Acid value, fatty acid composition, and calculated Iodine Value of oils extracted from corn germ (CG), distillers dried grains with soluble (DDGS), and centrifugally extracted thin stillage syrup (CS-1, CS-2, CS-3)

|  | CG | DDGS | CS-1 | CS-2 | CS-3 |
| --- | --- | --- | --- | --- | --- |
| Acid Value (mg KOH/g) | 10.7 ± 0.07 | 20.8 ± 0.36 | 28.3 ± 0.32 | 5.70 ± 0.13 | 6.88 ± 0.09 |
| FFA (% oleic acid) | 3.80 ± 0.03 | 7.42 ± 0.13 | 10.1 ± 0.11 | 2.03 ± 0.05 | 2.48 ± 0.05 |
| Fatty Acid Composition (%) | | | | | |
| 16:0 | 13.1 | 12.9 | 11.5 | 12.2 | 12.9 |
| 16:1 | 0.0 | 0.1 | 0.1 | 0.1 | 0.1 |
| 18:0 | 1.5 | 1.8 | 1.7 | 1.8 | 1.5 |
| 18:1 | 29.2 | 28.1 | 29.3 | 28.3 | 27.5 |
| 18:2 | 55.0 | 55.5 | 55.6 | 55.3 | 55.9 |
| 20:0 | 0.2 | 0.3 | 0.3 | 0.4 | 0.3 |
| 18:3 | 1.0 | 1.2 | 1.17 | 1.2 | 1.2 |
| 20:1 | 0.0 | 0.0 | 0.2 | 0.3 | 0.2 |
| Calculated iodine Value | 122.4 | 123.1 | 124.3 | 123.7 | 124.1 |

Fatty Acid Composition and Free Fatty Acids

The fatty acid compositions (Table 4) of all five oils were typical for corn oil. The Iodine Values ranged from 122.4 to 124.3. These results concur with other reports that the fatty acid composition of oil extracted from DDGS and thin stillage are similar to corn oil. The two oils (CS-1 and CS-2) that were centrifugally extracted from syrup from the raw starch ethanol production facilities had the lowest % FFA (2.03% and 2.48%, respectively). The oil recovered by centrifugation of syrup from the traditional dry grind ethanol production plant had the highest Acid Value, with 10.1% FFA. Other studies have reported FFA content of oil recovered by centrifugation of thin stillage ranging from 11.2-16.4%. These results indicate that the elimination of the cooking step in the raw starch process reduces the production of FFA. The oil extracted from DDGS using hexane had the second highest acid value (7.42% FFA). Winkler-Moser and Vaughn (2009) reported FFA content of 6.8% (w/w) in hexane Soxhlet extracted DDGS oil, while Moreau et al. (2010) reported FFA content ranging from 8-12% in DDGS that was extracted with hexane using accelerated solvent extraction. FFA content of DDGS extracts has been shown to vary widely depending on the extraction method and conditions and on the solvent used. The DDGS used in this study also came from a raw starch ethanol plant, so it might be expected to have lower FFA. However, high temperatures Content and Composition of Tocopherols, Tocotrienols, and Carotenoids Tocopherols are common in vegetable oils and are the primary antioxidants protecting most oils. With corn and other plants, the tocopherol and tocotrienol content will vary based upon factors including hybrid, growth conditions, post-harvesting and processing conditions, as well as the type of solvent used for extraction. Therefore, in this study little can be inferred about how processing practices affected tocopherol levels since each production facility and even each production run will have started with different batches of whole corn. Gamma- and alpha-tocopherol were the most prominent homologues detected in all five oils (Table 5), along with a small amount of delta-tocopherol, which is the typical tocopherol profile for corn oil. CG oil had the highest total concentration of tocopherols (1433.6 μg/g oil) followed by the hexane extracted DDGS (1104.2). The levels in the DDGS oil are similar to what was previously reported in hexane extracted DDGS from a conventional dry grind production facility. Tocopherols in corn are localized in the germ portion of the kernel, so the rest of the corn kernel contributes little to the tocopherol content. CS-1, CS-2, and CS-3 were all lower in alpha-tocopherol compared to CG and DDGS oils, but were similar to levels reported in oil extracted centrifugally from thin stillage (Moreau et al., 2010).

TABLE 5

Content of tocols and carotenoids, and the oxidative stability index (OSI) at 110° C., for oils extracted from corn germ (CG), distillers dried grains with solubles (DDGS), and centrifugally extracted thin stillage syrup (CS-1, CS-2, CS-3)

|  | CG | DDGS | CS-1 | CS-2 | CS-3 |
|---|---|---|---|---|---|
| Total Tocopherols (µg/g) | 1433.6 | 1104.2 | 1056.9 | 931.3 | 783.4 |
| Alpha-tocopherol | 213.8 | 295.6 | 164.5 | 160.4 | 123.2 |
| Gamma-tocopherol | 1185.4 | 760.8 | 852.7 | 742.0 | 640.0 |
| Delta-tocopherol | 34.3 | 47.8 | 39.7 | 28.8 | 20.2 |
| Total Tocotrienols (µg/g) | 235.6 | 1762.3 | 1419.6 | 1224.4 | 1175.2 |
| Alpha-tocotrienol | 21.9 | 471.9 | 328.5 | 243.6 | 269.4 |
| Gamma-tocotrienol | 165.6 | 1210.0 | 1063.6 | 963.4 | 880 |
| Delta-tocotrienol | 48.1 | 80.3 | 27.5 | 17.3 | 25.8 |
| Total Carotenoids (µg/g) | 1.33 | 75.02 | 129.48 | 61.1 | 85.0 |
| Lutein | 0.37 | 46.69 | 75.69 | 38.13 | 53.7 |
| Zeaxanthin | 0.4 | 24.16 | 45.58 | 16.78 | 23.7 |
| Beta-cryptoxanthin | 0.56 | 3.31 | 7.35 | 4.12 | 5.1 |
| Beta-carotene | ND[a] | 0.86 | 0.86 | 2.07 | 2.5 |
| OSI (hr) | 3.91 | 6.62 | 4.45 | 4.52 | 5.27 |

[a]Not detected

Tocotrienols are common in rice bran oil and palm oil, but are not abundant in most commercial vegetable oils. Their antioxidant activity is similar to tocopherols in bulk oil systems, but they also appear to have hypocholesterolemic, anti-cancer, and neuroprotective properties. The post-fermentation corn oils (DDGS, CS-1, CS-2, and CS-3) were higher in tocotrienol concentration compared to CG oil, because tocotrienols are found in the endosperm fractions, which are mostly removed during the fractionation of corn germ. Thus, despite having lower tocopherol concentration, all of the post-fermentation oils were higher in total tocopherol concentration compared to the CG oil.

The post-fermentation corn oils were much higher in carotenoids than the extracted corn germ oil as well. However, the concentration of carotenoids was substantially lower than the tocols in five oils (Table 5). As with tocotrienols, carotenoids are localized to the endosperm fraction of corn kernels. The main carotenoids in the oils were lutein and zeaxanthin, as well as lower quantities of beta-cryptoxanthin and beta-carotene. Carotenoid content and composition were similar to amounts found in DDGS oil in a previous study, however, Moreau et al. (2010) reported carotenoid content in centrifugally extracted thin stillage oil ranging from 295 to 405 µg/g oil. Carotenoids are substantially affected by corn hybrid, which may explain the discrepancy. Beta-carotene and beta-cryptoxanthin are both precursors to Vitamin A, while lutein and zeaxanthin are both protective against age-related macular degeneration and cataracts. Carotenoids have also been shown to have a number of beneficial physiological actions other than Vitamin A activity, including antioxidant activity, enhanced immune response, and chemoprotective activity against several types of cancer.

Content and Composition of Phytosterols

The content of total phytosterols in the three oils ranged from 1.5-2.0% (w/w) (Table 6). The post-fermentation corn oils were higher in total phytosterols compared to the CG oil because they include phytosterols and ferulate phytosterol esters from the bran and pericarp, in addition to the phytosterols from the germ portion of the corn kernel. The phytosterol composition is also different between CG oil and the post-fermentation corn oils. DDGS and CS-1, CS-2, and CS-3 oils had similar concentrations of the common phytosterols campesterol, stigmasterol, and sitosterol compared to CG oil. However, they had a much higher concentration of the two saturated phytosterols (phytostanols), campestanol and sitostanol. The high content of these phytostanols is due to their preferential esterification, in corn, to steryl ferulates, the contents of which are also shown in Table 6. Steryl ferulates are found in the inner pericarp of corn and other grains. The presence of a small amount of these compounds in the corn germ oil indicates that there may have been some contamination of the germ by some inner pericarp tissue, as it has been established that these compounds are unique to the aleurone layer of the pericarp. Phytosterols are highly valued as ingredients in functional foods due to their ability to lower blood cholesterol by blocking re-adsorption of cholesterol from the gut.

Steryl ferulates have been shown to retain the cholesterol lowering ability of phytosterols, and also have antioxidant activity due to the ferulic acid moiety.

TABLE 6

Content and compositions of phytosterols in oils extracted from corn germ (CG), distillers dried grains with solubles (DDGS), and centrifugally extracted thin stillage syrup (CS-1, CS-2, CS-3).

|  | CG | | DDGS | | CS-1 | | CS-2 | | CS-3 | |
|---|---|---|---|---|---|---|---|---|---|---|
|  | mg/g | %[a] | mg/g | % | mg/g | % | mg/g | % | mg/g | % |
| Total Phytosterols | 14.9 |  | 21.7 |  | 18.7 |  | 20.1 |  | 20.2 |  |
| Campesterol | 3.08 | 20.7 | 2.97 | 13.7 | 2.74 | 14.7 | 2.74 | 13.6 | 3.0 | 14.7 |
| Campestanol | 0.25 | 1.7 | 1.35 | 6.2 | 1.40 | 7.5 | 1.30 | 6.5 | 1.4 | 6.7 |
| Stigmasterol | 0.98 | 6.6 | 1.10 | 5.1 | 0.76 | 4.1 | 0.91 | 4.5 | 0.89 | 4.4 |
| Sitosterol | 9.04 | 60.9 | 10.3 | 47.5 | 8.77 | 46.9 | 9.36 | 46.5 | 9.3 | 46.1 |
| Sitostanol | 0.66 | 4.4 | 3.72 | 17.2 | 3.59 | 19.2 | 3.45 | 17.2 | 3.2 | 16.0 |
| Avenasterol | 0.54 | 3.7 | 0.93 | 4.3 | 0.86 | 4.6 | 0.94 | 4.7 | 1.0 | 5.2 |
| Cycloartenol | 0.28 | 1.9 | 0.71 | 3.2 | 0.59 | 3.2 | 0.74 | 3.7 | 0.73 | 3.6 |
| 24-methylene cycloartanol | ND[b] | 0 | 0.30 | 1.4 | ND | 0 | 0.34 | 1.7 | 0.30 | 1.5 |
| Citrostadienol | ND | 0 | 0.31 | 1.4 | ND | 0 | 0.31 | 1.6 | 0.36 | 1.8 |
| Steryl Ferulates (mg/g) | 0.58 | 3.9 | 3.42 | 15.7 | 3.15 | 16.8 | 3.38 | 16.8 | 3.35 | 16.6 |

[a]The weight percentage of total phytosterols
[b]Not detected

Oxidative Stability Index (OSI)

The oxidative stability of oils are affected by many factors, including fatty acid composition, concentration and stability of antioxidants in the oil, and the presence of prooxidant compounds, such as free fatty acids, lipid peroxides, or prooxidant metals. The Rancimat is an accelerated test (taking several hours to a day, depending on the oil and test temperature) used to establish the relative oxidative stability of oils, as measured by the induction time (called the oxidative stability index, OSI) for an oil to begin oxidizing under controlled temperature and air flow conditions. The OSI of the CG oil was lowest, while DDGS oil had the highest stability (Table 5), which corresponds to the lowest and the highest concentration of antioxidant tocopherols. CS-1 had a slightly lower OSI than CS-2 and CS-3 despite having a higher concentration of tocols; this may be explained by its higher content of FFA and higher initial peroxide value.

Conclusions

The fatty acid compositions of all five oils were typical for corn oil. Oil extracted from thin stillage in a raw starch production facility has lower FFA than from thin stillage from a conventional dry grind ethanol production facility. This is likely due to lower processing temperatures used in the raw starch process where the cooking stage is eliminated. All of the post-fermentation oils had higher concentrations of tocotrienols, carotenoids, phytosterols, and ferulate phytosterol esters compared to the corn germ oil. The increased concentrations of the antioxidant tocotrienols carotenoids, and steryl ferulates are likely responsible for their increased stability compared to corn germ oil.

Other Exemplary Embodiments

Also provided is a corn oil composition comprising unrefined corn oil having an ethyl ester content that is greater than about 7 weight percent; and optionally a moisture content of from about 0.02 to about 1 weight percent and/or an alkali metal ion and/or alkaline metal ion content of greater than 10 ppm up to about 1000 ppm. In one embodiment, the unrefined corn oil has a free fatty acid content of less than about 5 weight percent. In one embodiment, the unrefined corn oil has an ethyl ester content that is greater than 30 weight percent. In one embodiment, the unrefined corn oil has an insoluble content of less than about 1.5 weight percent. In one embodiment, the unrefined corn oil has a free fatty acid content of less than about 3 or less than about 2 weight percent. In one embodiment, the unrefined corn oil has a peroxide value of less than about 2 parts per million. The corn oil composition may include a lutein content of at least 50 mcg/g, a zeaxanthin content of at least 30 mcg/g, a cis-lutein/zeaxanthin content of at least 10 mcg/g, an alpha-cryptoxanthin content of at least 5 mcg/g, a beta-cryptoxanthin content of at least 5 mcg/g, an alpha-carotene content of at least 0.5 mcg/g, a beta-carotene content of at least 1 mcg/g, a cis-beta-carotene content of at least 0.1 mcg/g, an alpha-tocopherol content of at least 50 mcg/g, a beta-tocopherol content of at least 2 mcg/g, a gamma-tocopherol content of at least 300 mcg/g, a delta-tocopherol content of at least 15 mcg/g, an alpha-tocotrienol content of at least 50 mcg/g, a beta-tocotrienol content of at least 5 mcg/g, a gamma-tocotrienol content of at least 80 mcg/g, a delta-tocotrienol content of at least 5 mcg/g, or any combination thereof.

In one embodiment, a method for providing a corn oil composition with enhanced levels of ethyl ester includes obtaining a first aqueous layer from a corn fermentation residue; adjusting the pH of the first aqueous layer to provide a corn oil layer and a second aqueous layer; and separating the corn oil layer from the second aqueous layer to provide the corn oil composition having a free fatty acid content of less than about 2% or less than about 5% and has at least 10% w/w ethyl ester. In one embodiment, the first aqueous layer has a moisture content of between about 95% and about 60%. In one embodiment, the first aqueous layer comprises thin stillage. In one embodiment, the method further comprises evaporating the thin stillage prior to the step of adjusting the pH of the first aqueous layer. In one embodiment, the first aqueous layer comprises syrup. In one embodiment, adjusting the pH comprises adding a base. In one embodiment, adjusting the pH comprises adding a base selected from the group consisting of sodium hydroxide, potassium hydroxide, calcium hydroxide, or spent alkali wash solution. In one embodiment, the pH of the first aqueous layer is less than about 4 prior to the step of adjusting the pH of the first aqueous layer. In one embodiment, the pH of the first aqueous layer is about 3.5 prior to the step of adjusting the pH of the first aqueous layer. In one embodiment, the pH of the first aqueous layer is from about 7.5 to about 10 after adjusting the pH of the first aqueous layer. In one embodiment, the pH of the first aqueous layer is from about 8 to about 9 after adjusting the pH of the first aqueous layer. In one embodiment, the pH of the first aqueous layer is about 8.2 after adjusting the pH of the first aqueous layer. In one embodiment, obtaining the first aqueous layer from the corn fermentation residue comprises centrifuging. In one embodiment, obtaining the first aqueous layer from the corn fermentation residue comprises a) separating the first aqueous layer into a water layer and an emulsion layer; and b) adjusting the pH of the emulsion layer to provide a corn oil layer and a second aqueous layer. In one embodiment, obtaining the first aqueous layer from the corn fermentation residue to provide an emulsion layer and a first aqueous layer comprises centrifuging. In one embodiment, separating the corn oil layer from the second aqueous layer comprises centrifuging. In one embodiment, the corn oil layer comprises a free fatty acid content of less than about 2 weight percent. In one embodiment, the corn oil layer comprises a moisture content of from about 0.2 to about 1 weight percent. In one embodiment, the corn oil layer comprises an alkali metal ion and/or alkaline metal ion content of greater than 10 parts per million. In one embodiment, the corn oil layer has an insoluble content of less than about 1.5 weight percent. In one embodiment, the corn oil layer exhibits a peroxide value of less than about 2 parts per million. In one embodiment, the corn oil layer exhibits an oxidative stability of greater than about 4 hours at a temperature of about 110° C.

The invention will be further described with respect to the following examples.

Example 1

Materials and Methods

A raw starch simultaneous saccharification and fermentation (SSF) process was employed. #2 yellow corn was milled with a hammer mill using 0.5 mm to 2.0 mm screens into whole corn flour. Raw starch hydrolyzing enzymes were used to breakdown the starch in the flour into monomeric glucose which was then metabolized by yeast to produce ethanol. An esterase was added during fermentation to enhance ethyl ester content in the corn oil produced. A yeast propagation culture media was used for propagating yeast. A preblend derived from recycled ethanol biorefinery makeup water and including diluted and partially clarified thin stillage was used as a nutrient source for yeast fermentation. The percent solids and percent moisture of the corn flour and preblend used in fermentation was determined by mass loss on drying in a 100° C. oven. The fat content of the flour was determined by accelerated fat extraction utilizing an extraction system (Dionex ASE 350) with hexane as the extracting solvent.

Yeast Propagation and Conditioning 1-3 colonies of *Saccharomyces cerevisiae* yeast isolated off a yeast extract and soy peptone containing 3% glucose (YP medium) agar plate, or alternatively slurried dry yeast or creme yeast, were used to inoculate 50 mL of YP culture media in a shake flask. The flask was shaken in a water bath at 150 rpm for approximately 17 hours at 30° C. to propagate the yeast.

A conditioning medium was prepared in a 1 L Pyrex bottle capped with a lid with a hole to release carbon dioxide produced during fermentation. Corn flour was added and slurried to a final solids loading of 32%. The slurry was pH adjusted to 4.5 using 10% (% v/v) sulfuric acid. In addition, an appropriate amount of antibiotic, urea, a cocktail of α-amylases and glucoamylases are added to the slurry according to U.S. Pat. No. 7,842,484. Propagated yeast culture at approximately 1.0E+07 cells mL$^{-1}$ was added to the fermenter to give a final number of 7.0E+08 yeast cells in the fermenter. The conditioning fermentation was allowed to ferment in a water batch shaking at 150 rpm at 30-32.2° C. for eight hours.

Fermentation

Fermentation was carried out as in the conditioning step according to U.S. Pat. No. 7,842,484 unless stated otherwise. For fermentation, a 500 mL Pyrex bottles were used for a total fermentation volume of 250 mL. The corn flour was slurried with preblend to a total percent solids of 36.5%. In addition, an esterase such as a lipase (Novozymes Eversa Transform 2.0), was added to the slurry as well. The dose of the enzyme is based upon the total weight of corn fat present in the fermenters. A typical dose is 0.4% (% w/w), although experiments with 0.04% and 4.00/0 were performed as well. Fermentation in the bottles was allowed to progress for 88 hours, at which point the beer was sampled and harvested for oil analysis.

Oil Extraction and Analysis

Oil Extraction

The oil was extracted from the entire volume of beer remaining after sampling. First, the beer was centrifuged at approximately 4° C. for 20 minutes at 4500 rpm in a bench centrifuge. The resulting floating oil emulsion was then removed. The emulsion was put in 50 mL conical tubes to which approximately 10-20 mL of chloroform was added and vortexed. Then 10-20 mL of deionized water was also added to help with separation. The 50 mL tubes were then centrifuged at 3000 rpm for five minutes. The bottom layer (chloroform+oil) was pulled off and put into tared glass vials and inserted into a turbovap to evaporate off the solvent. The resulting dry oil was then used to quantify fatty acid ethyl esters.

Fatty Acid Ethyl Ester Determination by Gas Chromatography

Approximately 50 mg of the extracted oil was added to a 10 mL volumetric flasks to which xylene was added to the 10 mL graduation. External standards including ethyl palmitoleate, ethyl oleate, and ethyl linoleate were used to generate standard curves to determine the amount of each individual fatty acid ethyl ester present in the extracted corn oil. Standard concentrations used ranged from 0.02 mg mL$^{-1}$ to 0.40 mg mL$^{-1}$. The samples and standards were run on a gas chromatograph (GC) equipped with a split/splitless injector (with splitless glass liner) and flame ionization detector (FID). Also, the GC was equipped with a Phenomenex Zebron ZB-Waxplus column (30 m L×0.32 mm ID×0.25 μm df). Analysis was conducted by injecting 1 μL of the sample into the inlet held at 250° C. The oven was initially set at 170° C. and followed an oven temperature gradient of 2° C. min$^{-1}$ up to 200° C. holding for 15 minutes, followed by a temperature gradient of 5° C. min$^{-1}$ up to 230° C. holding for nine minutes. The detector was maintained at a temperature of 250° C. Hydrogen was used as the carrier gas and the flow was controlled in constant flow mode at 1.80 mL min$^{-1}$.

Major ethyl esters in corn oil are ethyl palmitate, ethyl stearate, ethyl oleate, ethyl linoleate, and ethyl linolenate. In one embodiment, the ethyl esters include about 5% w/w to about 35% w/w ethyl palmitate, about 1% w/w to about 5% w/w ethyl stearate, about 10% w/w to about 30% w/w ethyl oleate, about 40/o w/w to about 60% w/w ethyl linoleate, and about 1% w/w to about 3% w/w ethyl linolenate of FAEE. In one embodiment, the ethyl esters include about 5% w/w to about 22% w/w ethyl palmitate, about 1% w/w to about 5% w/w ethyl stearate, about 23% w/w to about 30% w/w ethyl oleate, about 53% w/w to about 60% w/w ethyl linoleate, and about 1% w/w to about 2% w/w ethyl linolenate of FAEE. In one embodiment, the ethyl palmitate is about 23% w/w to about 35% w/w, ethyl stearate is about 1% w/w to about 5% w/w, ethyl oleate is about 10% w/w to about 22% w/w, ethyl linoleate is about 40% w/w to about 52% w/w, and ethyl linolenate is about 2% w/w to about 3% w/w of FAEE. In one embodiment, the ethyl palmitate is about 23% w/w to about 35% w/w, ethyl stearate is about 1% w/w to about 5% w/w, ethyl oleate is about 10% w/w to about 22% w/w, ethyl linoleate is about 40% w/w to about 61% w/w, and ethyl linolenate is about 2% w/w to about 3% w/w of FAEE With the aforementioned instrument parameters, ethyl palmitate would elute around 11 minutes, ethyl stearate around 16.5 minutes, ethyl oleate around 17 minutes, ethyl linoleate around 18 minutes, and ethyl linolenate around 19.5 minutes. A standard curve of each ethyl ester is obtained to give the slope and y-intercept for quantitation. Ethyl palmitate concentration is determined by the ethyl palmitoleate standard curve, ethyl stearate and ethyl oleate concentration are determined by the ethyl oleate standard curve, and ethyl linoleate and ethyl linolenate concentrations are determined from the ethyl linoleate standard curve. The total FAEE content of each sample is determined using the equation below.

$$\% \ FAEE \ (\% \ mg/mg) = \sum \frac{A_x - y_{int} \cdot 10}{S \cdot m}$$

Where:
- $A_x$=Area corresponding to the peaks for the individual esters
- $Y_{int}$=y-intercept of the linear regression
- S=Slope of the linear regression
- m=Mass of the sample, in milligrams Example 2

Conventional fermentation was carried out with a cooking liquefaction step. In liquefaction, 500 mL Pyrex bottles were used for a total volume of 250 mL of corn slurry. The corn was slurried with preblend to a total percent solids of 32.5%. The slurry was not pH adjusted for liquefaction. An alpha amylase was added to the slurry at approximately 0.14% (% v/v) by total volume of slurry. The bottles were then heated for 90 minutes at 85° C. in a shaking water bath. After liquefaction, the slurry was prepared for fermentation. Fermentation was carried out as in the conditioning step according to U.S. Pat. No. 7,842,484. For fermentation, 500 mL Pyrex bottles were used for a total fermentation volume of 250 mL. The liquefied starch was slurried with preblend to a total percent solids of 36.5%. In addition, an esterase such as a lipase, was added to the slurry as well. The dose of the enzyme is based upon the total weight of corn fat present in the fermenters. A typical dose is 0.4% (% w/w), although experiments with 0.040 and 4.0% were performed as well. Fermentation in the bottles was allowed to progress for 88 hours, at which point the beer was sampled and harvested for oil analysis.

Corn oil extracted from ethanol fermentation is mostly in the form of triacylglyceride and is typically sold into limited markets (animal feed, food grade or bio-diesel) due to lack of industrial utility. In order to increase the utility of the corn oil, an esterase can be added directly to fermentation to facilitate chemical modification of the corn oil to give it unique properties, specifically by increasing the ethyl ester content. Increased ethyl ester content lends to lower viscosity which is desirable in asphalt rejuvenation and performance grade composition. The transesterification/esterification of corn triacylglycerides/free fatty acids with ethanol produced during fermentation can have several added benefits such as increased oil yield, increase yeast vitality due to liberation of free fatty acids and glycerol, as well as enhanced starch utilization.

Figure 7:
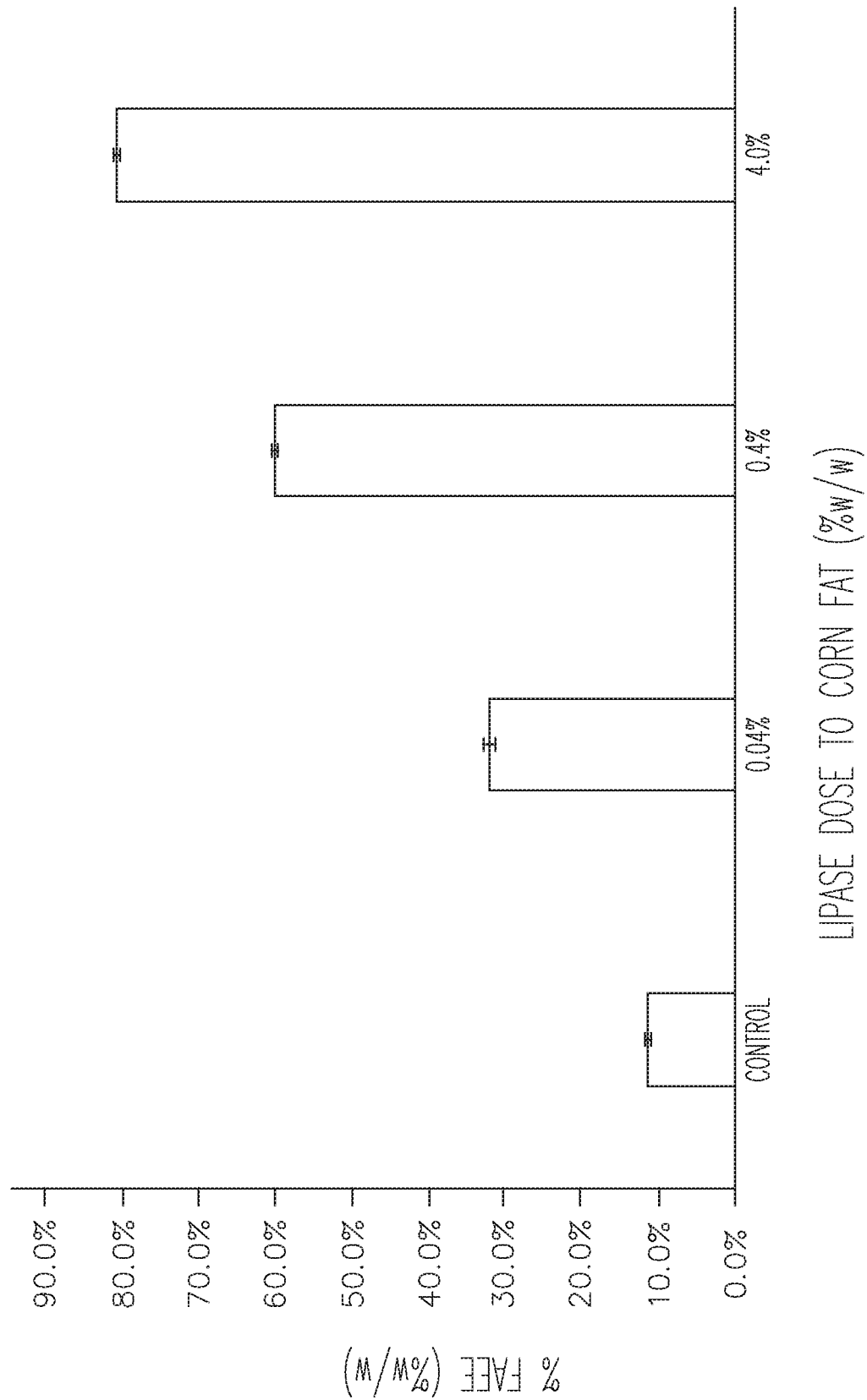
FIG. 7 shows that addition of lipase at the beginning of BPX fermentation increases the level of FAEE in corn oil extracted at the end of fermentation. The various enzyme doses of control (0.0%), 0.04%, 0.4%, and 4.0% are based upon lipase weight added to weight of corn fat available in the fermenter. Each dose was performed in duplicate.
Figure 8:
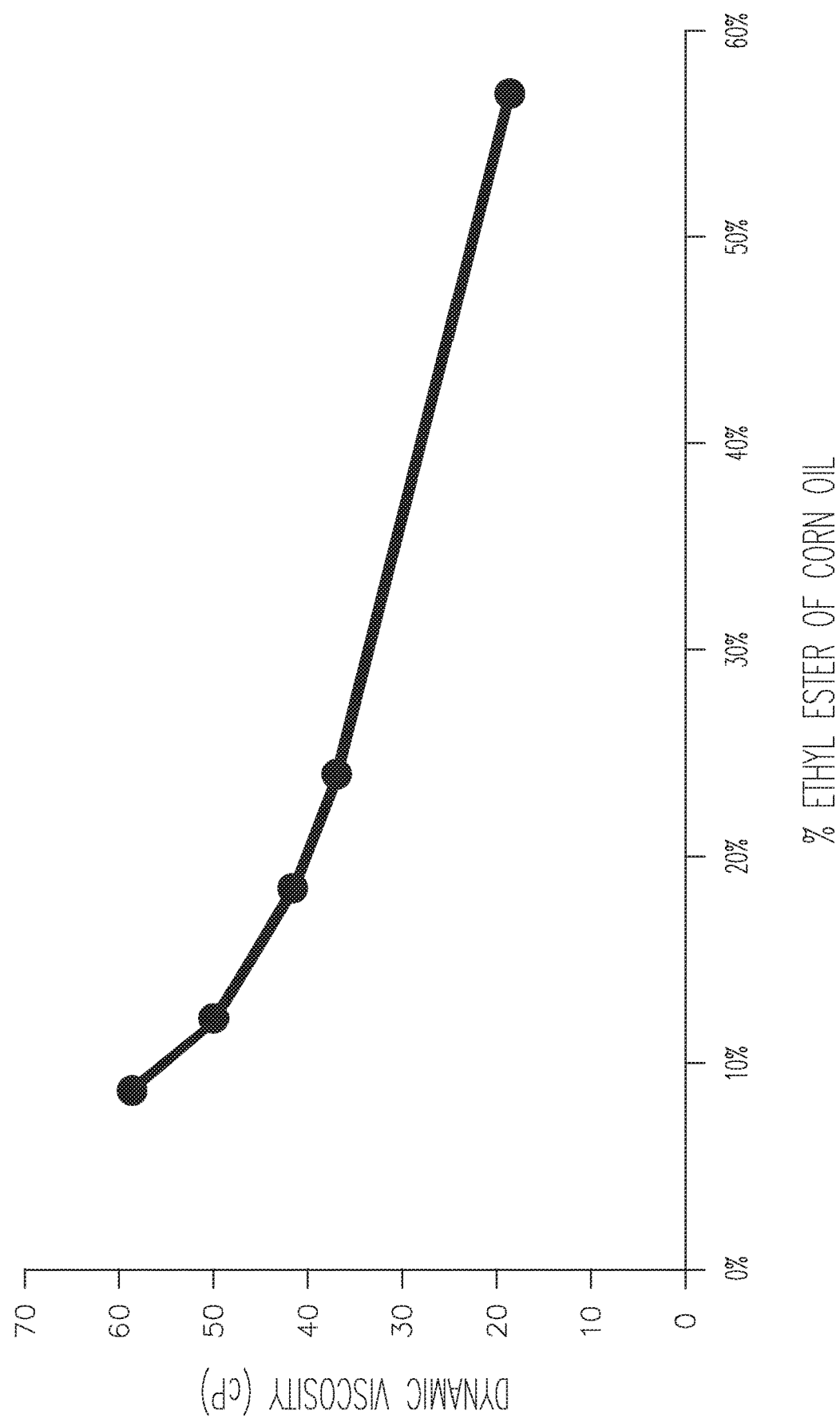
FIG. 8 shows that reduction of viscosity as a function of ethyl ester content in corn oil. The dynamic viscosity of corn oil at 25° C. is reduced as ethyl ester concentration is increased. Data was obtained with a Brookfield viscometer.
Figures 9, 10:
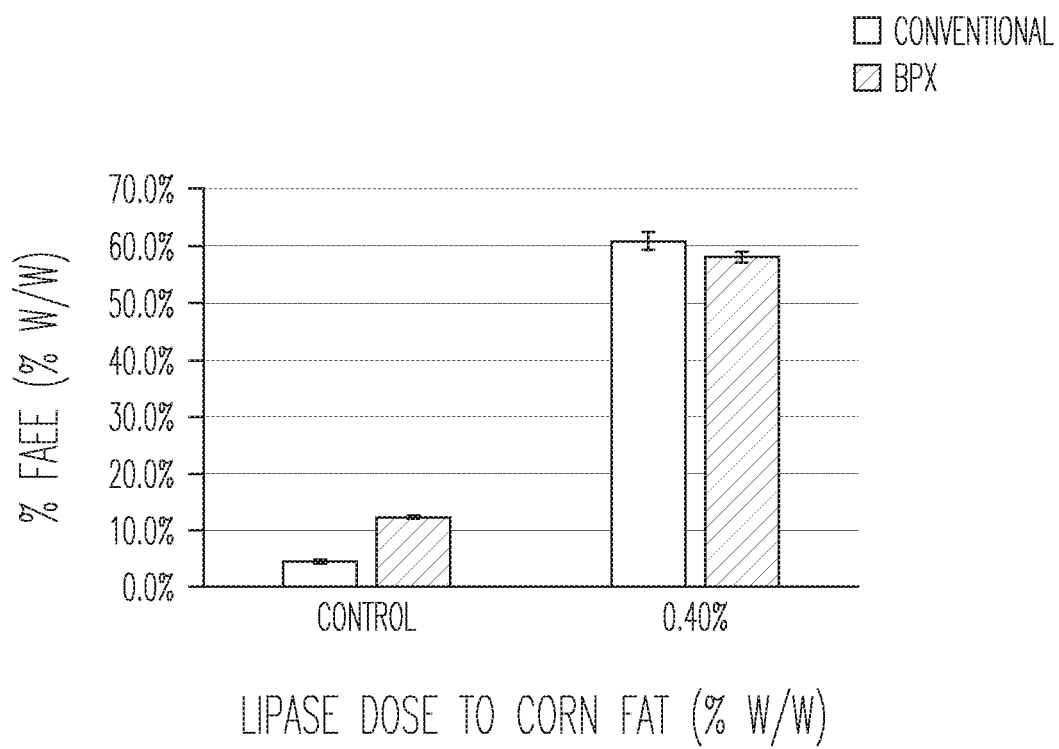
FIG. 9 illustrates fatty acid ethyl ester content of corn oil extracted from conventional and BPX fermentations with and without lipase addition. N=2 for each experiment.
FIG. 10 shows the effect of different lipases on extracted corn oil fatty acid ethyl ester content when added to BPX fermentation. N=2 for each experiment.
Figure 11A:
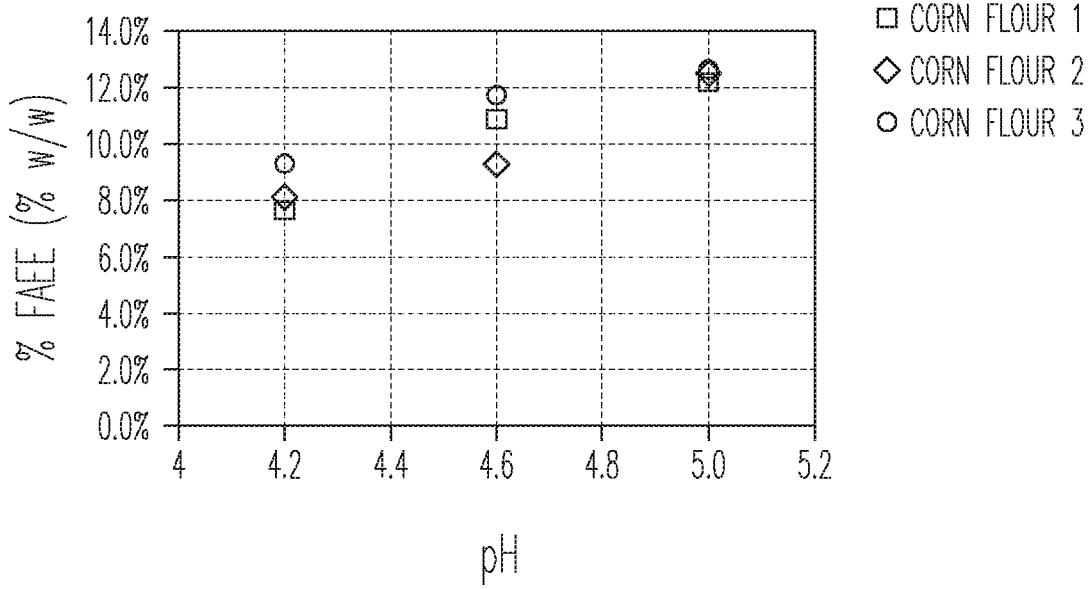
FIG. 11A. Effect of pH and corn flour source in BPX fermentation without added lipase on corn oil fatty acid ethyl ester content.
Figure 11B:
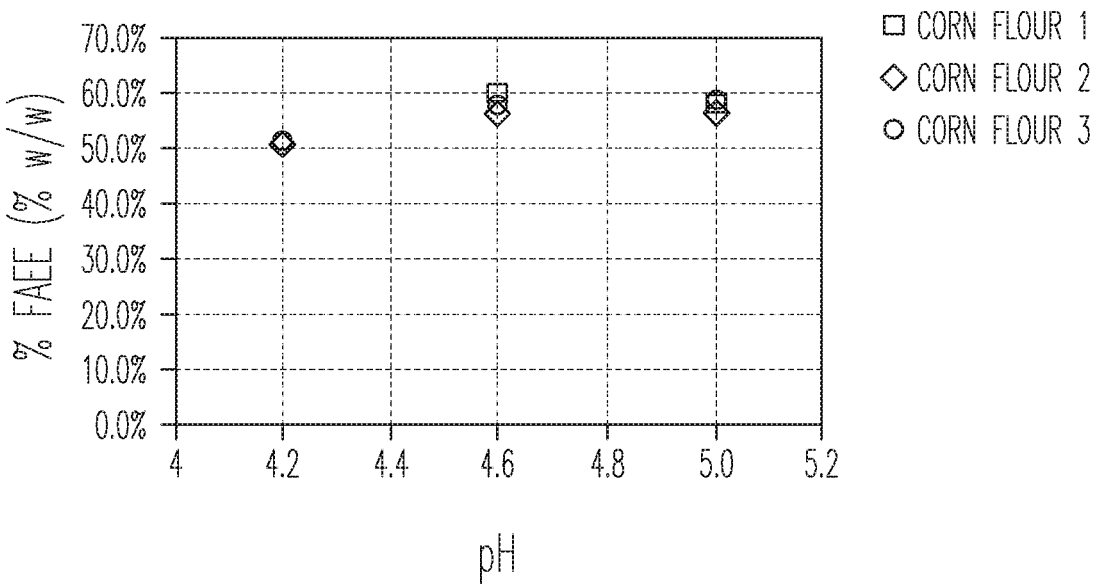
FIG. 11B. Effect of pH and corn flour source in BPX fermentation with lipase on corn oil fatty acid ethyl ester content.
Figure 12:
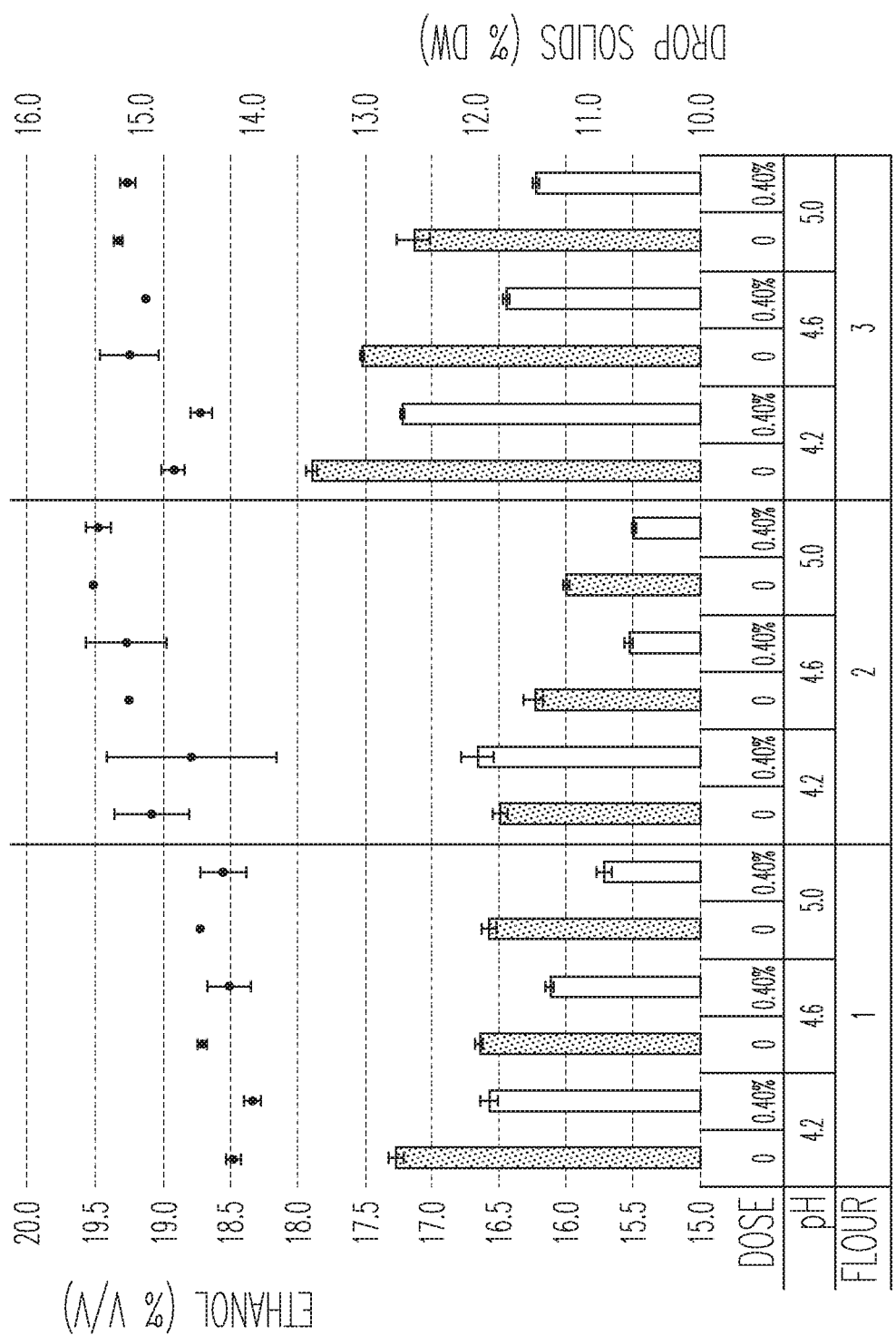
FIG. 12 illustrates the effect of lipase on percent solids and ethanol titer at BPX fermentation drop.

In an embodiment, an exogenous esterase, e.g., a lipase, was added to the fermentation to increase ethyl ester content of extracted oil over levels obtainable without adding the exogenous esterase. This was shown to work with both raw starch processes and cooked starch processes. The FAEE content can be increased above 60% (% w/w). FIG. 7 shows that the FAEE content of the extracted corn oil can be increased beyond 80% w/w.

Thus, in order to increase the utility of the corn oil, an esterase such as a lipase can be added directly to the fermentation to facilitate chemical modification of the corn oil to give it unique properties, specifically by increasing the ethyl ester or FAEE content, respectively.

It was surprising that endogenous corn lipases/esterases appear to catalyze the reaction of ethanol produced throughout fermentation with corn oil present in corn flour to produce fatty acid ethyl esters (FAEE). Further, it was surprising that the FAEE content in the extracted corn oil could be increased by adding exogenous lipase/esterase, e.g., triacylglycerol lipase, into the fermentation. This is unexpected because the excess of water relative to ethanol in fermentation should push the reaction toward production of free fatty acids (FFA) rather than FAEE since water would be available to hydrolyze ester bonds present in triacylglycerides, diacylglycerides, monoacylglycerides, and/or FAEE to form FFA. In addition or in lieu of esterase addition during fermentation, esterase may be added to the beerwell.

REFERENCES

Bennert et al., *Transp. Res. Rec. J. Transp. Res. Board*, 2574:1 (2016).
Cox, Asphalt Binders Containing a Glyceride and Fatty Acid Mixture and Methods for Making and Using Same. (2016).
D'amore and Stewart, *Enzyme Microb. Technol.*, 9:322 (1987).
D'amore et al., *CRC Rev. Biotechn.*, 9:287 (1989).
DiCosimo et al., In situ expression of lipase for enzymatic production of alcohol esters during fermentation (2014).
Golalipour, Investigation of the Effect of Oil Modification on Critical Characteristics of Asphalt Binders. *PhD Thesis* (2013).
Grichko, Fermentation processes and compositions (2004).
Hughes et al., *J. Assoc. Lab. Autom.*, 16:17 (2011).
Lackey & James, Biodiesel cutback asphalt and asphalt emulsion. (2004).
Layfield et al., *Master Brew. Assoc. Am.*, 52 (2015).
Mogawer et al., *Road Mater. Pavement Des.*, 14:193 (2013).
Moreau et al., *J. Am. Oil Chem. Soc.*, 88:435 (2010)
Seidel & Haddock, *Constr. Build. Mater.*, 53:324 (2014).
van den Berg et al., *Biotechol. Bioeng.*, 110:137 (2013).
Zaumanis et al., *Constr. Build. Mater.*, 71:538 (2014).
Winkler et al., *J. Agric. Food Chem.*, 55:6482 (2007).
Winkler-Moser and Vaughn, *J. Am. Oil Chem. Soc.* 86:1073 (2009).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method for enhancing properties of vegetable oil obtained from ground vegetable material, comprising:
providing a first composition comprising water, ground vegetable material, and vegetable fat;
enzymatically saccharifying a portion of the ground vegetable material to sugar;
fermenting the sugar to form a second composition comprising ethanol, water, ground vegetable material and vegetable fat; and
isolating vegetable oil from the second composition,
wherein an exogenous esterase is combined with the first composition and/or the second composition in an amount from 0.001 to 0.4% w/w of the weight of the vegetable fat, and wherein the isolated vegetable oil has a fatty acid ethyl ester content that is greater than 2% w/w of the total weight of the isolated vegetable oil.

2. The method of claim 1, wherein the fatty acid ethyl ester content is greater than 5% w/w of the total weight of the isolated vegetable oil.

3. The method of claim 1, wherein the fatty acid ethyl ester content is greater than 10% w/w of the total weight of the isolated vegetable oil.

4. The method of claim 1, wherein the fatty acid ethyl ester content is greater than 30% w/w of the total weight of the isolated vegetable oil.

5. The method of claim 1, wherein the esterase is in an amount that is up to 0.01% w/w of the weight of the vegetable fat.

6. The method of claim 1, wherein the esterase is in an amount that is up to 0.04% w/w of the weight of the vegetable fat.

7. The method of claim 1, wherein the esterase is in an amount that is from 0.01% to 0.4% w/w of the weight of the vegetable fat.

8. The method of claim 1, wherein the exogenous esterase is combined with both the first and second composition.

9. The method of claim 1, wherein the first composition comprises 20 to 50% wt-% of the ground vegetable material.

10. A method to decrease free fatty acids in vegetable oil obtained from ground vegetable material, comprising:
providing a first composition comprising water, ground vegetable material, and vegetable fat;
enzymatically saccharifying a portion of the ground vegetable material to sugar;
fermenting the sugar to form a second composition comprising ethanol, water, ground vegetable material and vegetable fat; and
isolating vegetable oil from the second composition,
wherein an exogenous esterase is combined with the first composition and/or the second composition in an amount from 0.001 to 0.4% w/w of the weight of the vegetable fat, and wherein the isolated vegetable oil has a decreased free fatty acid content relative to a corresponding composition obtained from the same method and under the same conditions and with the same materials except that lacks the exogenous esterase.

11. The method of claim 10, wherein the fatty acid ethyl ester content is greater than 2% w/w of the total weight of the isolated vegetable oil.

12. The method of claim 10, wherein the fatty acid ethyl ester content is greater than 7% w/w of the total weight of the isolated vegetable oil.

13. The method of claim 10, wherein the esterase is in an amount that is up to 0.01% w/w of the weight of the vegetable fat.

14. The method of claim 10, wherein the esterase is in an amount that is from 0.01% to 0.4% w/w of the weight of the vegetable fat.

15. A method to alter the viscosity of vegetable oil obtained from ground vegetable material, comprising:
providing a first composition comprising water, ground vegetable material, and vegetable fat;
enzymatically saccharifying a portion of the ground vegetable material to sugar;
fermenting the sugar to form a second composition comprising ethanol, water, ground vegetable material and vegetable fat; and
isolating vegetable oil from the second composition,
wherein an exogenous esterase is combined with the first composition and/or the second composition in an amount from 0.001 to 0.4% w/w of the weight of the vegetable fat, and wherein the isolated vegetable oil has an altered viscosity relative to a corresponding composition obtained from the same method and under the same conditions and with the same materials except that lacks the exogenous esterase.

16. The method of claim 15, wherein more than 50% of the ground vegetable material is capable of passing through a 0.5 mm screen.

17. The method of claim 15, wherein the pH is maintained in the range of 3 to 6 during the fermenting step.

18. The method of claim 15, wherein the pH is maintained in the range of 3 to 6 and the temperature is maintained in the range of 25° C. to 40° C. during the fermenting step.

* * * * *